(12) United States Patent
Hanson

(10) Patent No.: US 11,735,301 B2
(45) Date of Patent: Aug. 22, 2023

(54) COMPUTATIONAL REDUCTION VACCINE FOR COVID-19 ORIGINATING FROM CIVET SARS, BAT SARS, BETACOV BTRS, BETACOV BTRI, AND NEOROMICIA

(71) Applicant: Matthew Vernon Hanson, Cambridge, MA (US)

(72) Inventor: Matthew Vernon Hanson, Cambridge, MA (US)

( * ) Notice: Subject to any disclaimer, the term of this patent is extended or adjusted under 35 U.S.C. 154(b) by 339 days.

(21) Appl. No.: 17/137,209

(22) Filed: Dec. 29, 2020

(65) Prior Publication Data

US 2022/0208325 A1    Jun. 30, 2022

(51) Int. Cl.
*A61K 39/215*    (2006.01)
*C07H 21/02*    (2006.01)
*C07H 21/04*    (2006.01)
*G16H 20/10*    (2018.01)
*C12N 7/00*    (2006.01)

(52) U.S. Cl.
CPC ............... *G16H 20/10* (2018.01); *C12N 7/00* (2013.01); *A61K 39/215* (2013.01); *C07H 21/02* (2013.01); *C07H 21/04* (2013.01); *C12N 2770/20021* (2013.01); *C12N 2770/20034* (2013.01)

(58) Field of Classification Search
CPC ............ C12N 7/00; C12N 2770/20021; C12N 2770/20034
See application file for complete search history.

*Primary Examiner* — Nicole Kinsey White
*Assistant Examiner* — Ruixue Wang

(57) ABSTRACT

A vaccine candidate is herein described comprised by statistically significant DNA fragments related to Civet SARS, Bat Sars, and BtRs BetaCov, BtRI BetaCov, and Neoromicia resulting in three types of compositions: 1) a composition of statistically significant DNA fragments, 2) a composition of RNA transcripts corresponding to the statistically significant DNA fragments, and 3) a computational reduction composition wherein the DNA fragments are fully or partially subtracted from a base organism, resulting in a synthetic organism which has a high statistical likelihood of problematic functions being partially or fully removed.

3 Claims, 7 Drawing Sheets

Specification includes a Sequence Listing.

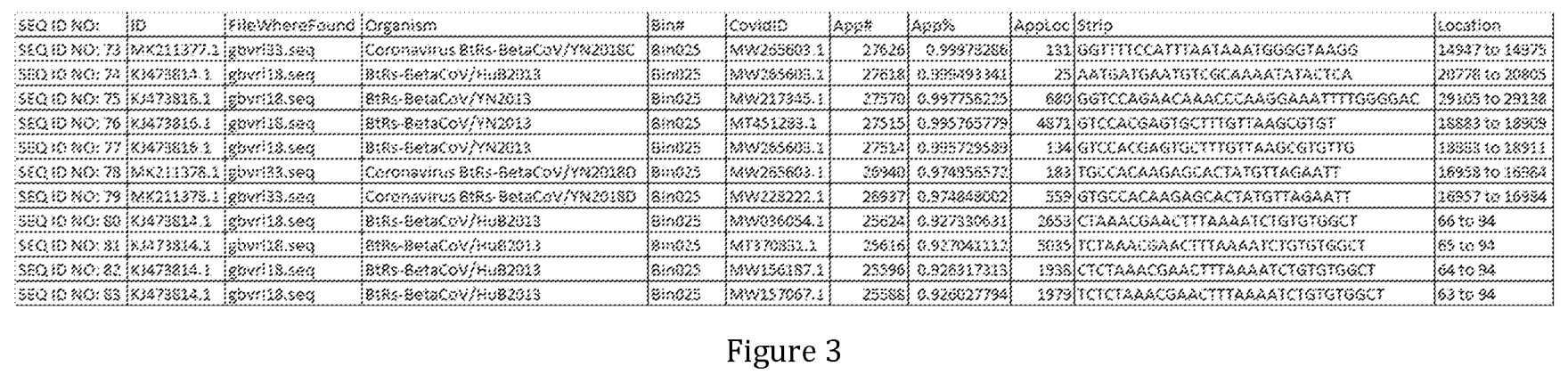

| SEQ ID NO: | ID | FileWhereFound | Organism | Bin# | CovidID | App# | App% | AppLoc | strip | Location |
|---|---|---|---|---|---|---|---|---|---|---|
| SEQ ID NO: 73 | MK211377.1 | gbvrl33.seq | Coronavirus BtRs-BetaCoV/YN2018C | Bin025 | MK211803.1 | 276.26 | 0.999732836 | 131 | GGTTTTCCATTTA

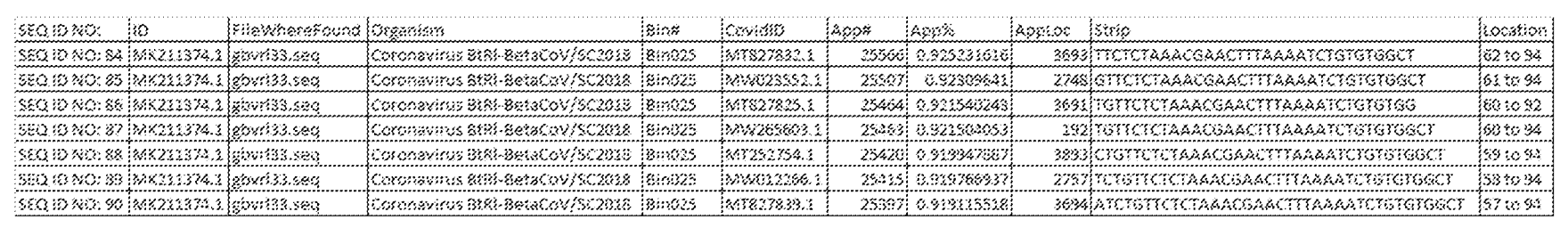

| SEQ ID NO: | ID | FileWhereFound | Organism | Bin# | CoviID | App# | App% | AppLoc | Strip | Location |
|---|---|---|---|---|---|---|---|---|---|---|
| SEQ ID NO: 84 | MK211374.1 | gbvrl33.seq | Coronavirus BtRl-BetaCoV/SC2018 | Bin025 | MT872832.1 | 255661 | 0.925331616 | 2692 | TCTCTAAACGAACTTAAA

| SEQ ID NO: | ID | FileWhereFound | Organism | Bin# | CovidID | App# | App% | AppLoc | Strip | Location |
|---|---|---|---|---|---|---|---|---|---|---|
| SEQ ID NO: 91 | KC869678.4 | gbvrl16.seq | Coronavirus Neoromicia/PML-PHE1/RSA/2011 | Bin025 | MW265603.1 | 27489 | 0.994824841 | 135 | GTCTTTATTTCACCTTATAATTCACAGA | 17764 to 17792 |
| SEQ ID NO: 92 | KC869678.4 | gbvrl16.seq | Coronavirus Neoromicia/PML-PHE1/RSA/2011 | Bin025 | LR897977.1 | 27489 | 0.994824841 | 1238 | TCTTTATTTCACCTTATAATTCACAGA | 17765 to 17792 |

…

COMPUTATIONAL REDUCTION VACCINE FOR COVID-19 ORIGINATING FROM CIVET SARS, BAT SARS, BETACOV BTRS, BETACOV BTRI, AND NEOROMICIA

BACKGROUND OF THE INVENTION

The present invention focuses on a computational reduction vaccine for Covid-19 with reduction fragments related to Civet Sars, Bat Sars, BetaCov RtRs, BetaCov BtRI, and Neoromicia.

A computational reduction vaccine may be defined herein as a vaccine candidate which is arrived at by removing various non-repetitive fragments in a virus or bacteria first computationally, then via Crispr in an actual "Super-Organism" (an organism which contains all, or the majority, of those fragments), and then utilizing the remaining organism as a traditional "live" or "dead" vaccine, which even though marginally computationally reduced, is still recognizable by the human immune system as an invader and therefore provokes a useful immune response. That immune response then shields the recipient from the actual virus going forwards.

It is now possible via Python modules such as Numpy (numerical Python) and Biopython (a module specifically designed for computationally manipulating DNA sequences), to analyze in great detail and with great speed thousands, or even millions of sequence records available through the NIH GenBank databases.

Those computational methods are not herein described, but the statistical analysis in the tables in the Drawings will illustrate the efficacy of the method in determining the frequency of various structures, as well as the ability to track those structures though time. It is along those two lines—frequency of appearance, and consistency of appearance, across an entire genetic database that one can derive vaccine candidates computationally.

The traditional way to do this would be to remove each fragment or structure via Crispr one by one and test the resulting organism for problematic function. Once problematic function was discovered and removed the resulting live or dead virus would be used in a vaccine. However, in the case of Covid-19, where solutions are demanded in shorter time frames, it is more efficient to simply remove all potential problematic function fragments via various fragment length groups (as seen in two other patent applications by this inventor) or via matches to related organisms (as is done here) in order to create one or two potential vaccine candidates instead of hundreds.

BRIEF DESCRIPTION OF SEVERAL VIEWS OF THE DRAWINGS

FIGS. 1-5 are a series of tables of computational fragment reductions from Covid-19 which are related to Civet Sars (FIG. 1), Bat Sars (FIG. 2), BetaCov RtRs (FIG. 3), BetaCov RtRI (FIG. 4) and Neoromicia (FIG. 5). Column headers are described below.

DETAILED DESCRIPTION OF THE INVENTION

Figure 6:
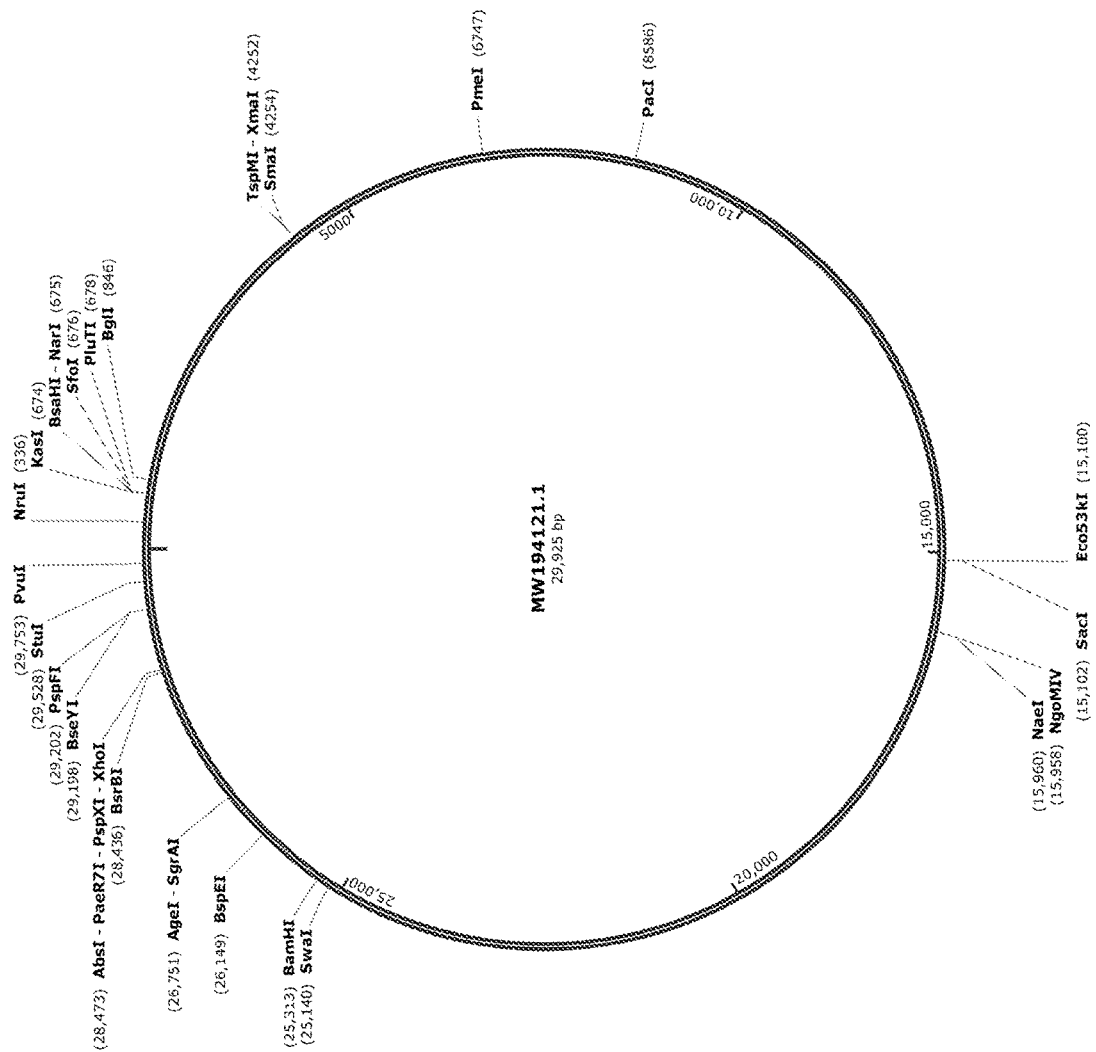
FIG. 6 is a SnapGene circular view of Covid-19 sample MW194121.1 from which this vaccine is derived.
Figure 7:
FIG. 7 is the same SnapGene circular view of MW194121.1 with the fragments in the tables removed.

There are several types of vaccines. This invention introduces a new type of vaccine which is a computationally derived reductive vaccine. A computationally derived reductive vaccine utilizes statistical computation to arrive at a list of fragments which can then be removed from live viruses or bacteria via Crispr to arrive at "neutered" versions which can then form the basis for the vaccine.

Computational reduction in this case may be defined as non-laboratory computational reduction of organisms into fragments, which then can be assessed on the basis of frequency across an entire range of similar organisms as well as computationally tested to confirm that those structures are unique to the virus or bacteria in question. The particulars of the method of discovery for these fragments is proprietary.

Figure 1:
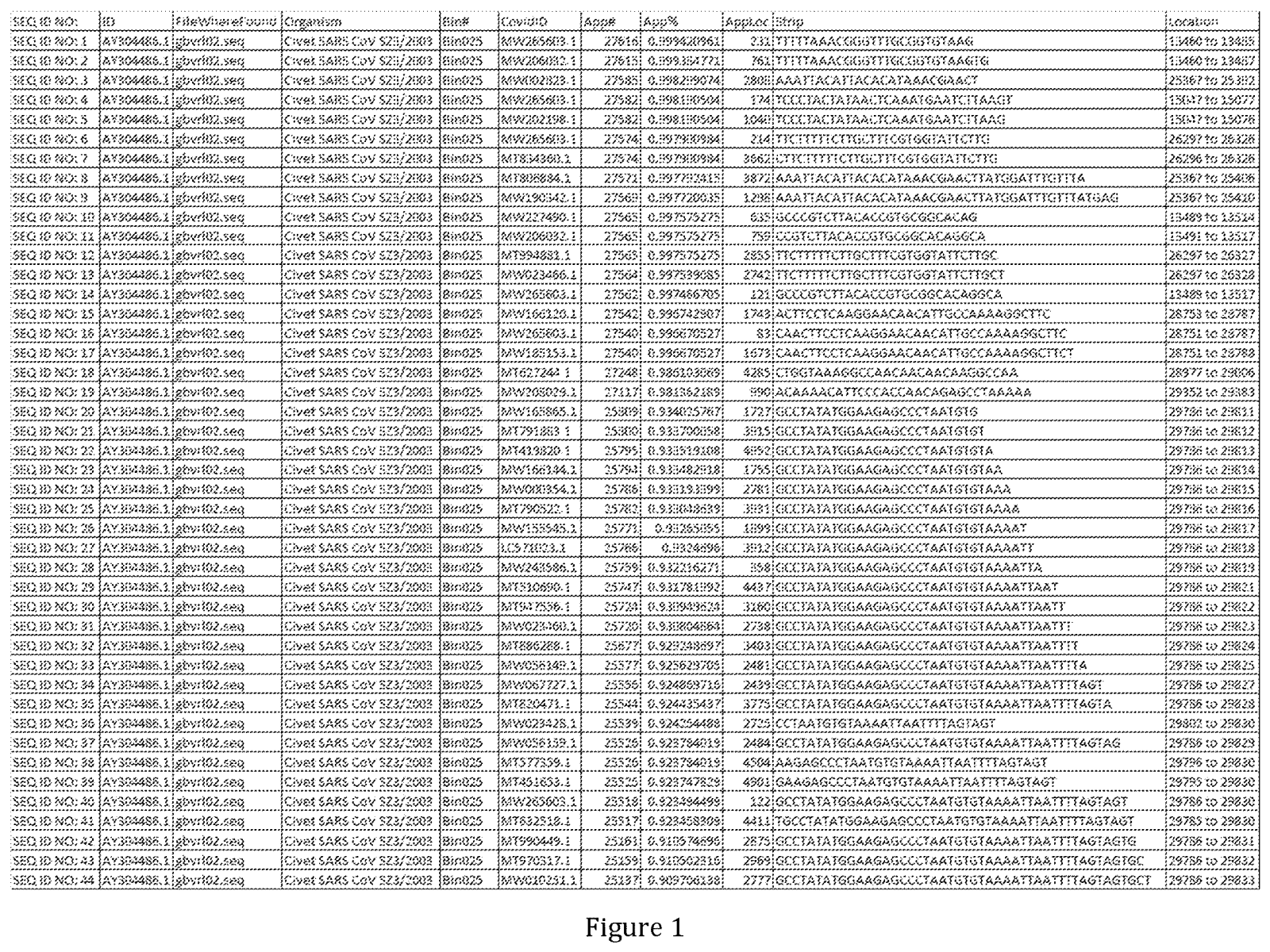
Figure 2:
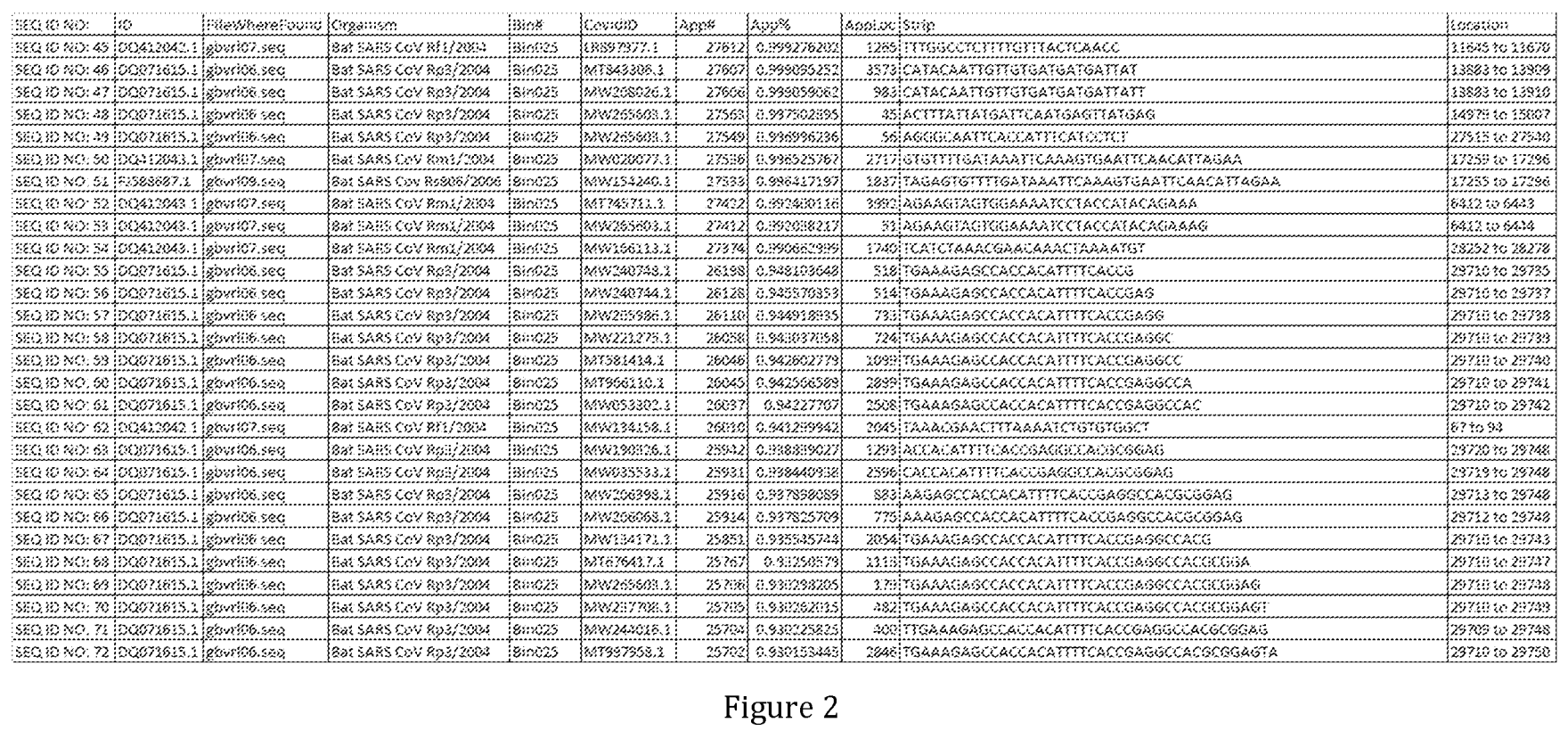

What is not proprietary is the statistical analysis of the fragments which are outlined in FIGS. 1-5. In the case of this particular vaccine candidate, the fragments which are included are related to Civet Sars, Bat Sars, BetaCov RtRs and BetaCov RtRI and appear in the NIH Covid-19 database greater than 90% of the time. The Covid-19 database "snapshot" from which the fragments in this patent were selected was taken on Nov. 18, 2020. That database is available upon request.

The result of this patent is relatively simple. When a Super Organism or Covid-19 sample which contains all, or most, of the fragments outlined in FIGS. 1-5 is found, that Super Organism can then be genetically modified in a laboratory using Crispr to remove those fragments. Once all those fragments are removed from the organism, it can then be tested in a laboratory to see if problematic function remains. "Problematic function" in the case of Covid-19 is two-fold: functions of the virus which have caused high transmissibility rates, and functions of the virus which cause high mortality rates. It may take us years to figure out exactly what those functions are and where they appear exactly on the genetic assay. This patent provides a shortcut by simply removing all of the most likely candidates for those problematic functions by identifying fragments which appear often enough not to be considered mutations (i.e. fragments only appearing in one or two samples).

The scan of the entire database of Covid-19 provides a total of 92 fragments related to Civet Sars, Bat Sars, BetaCov RtRs and BetaCov RtRI, and Neoromicia which appear more than 90% of the time across the entire Nov. 18, 2020 Covid-19 database.

Those 92 fragments are listed in a series of Excel tables in the Drawings. Each table header contains the following information going from left to right: the SEQ ID NO as found in the Sequence file (SEQ ID NO:); the Genbank virus file where the match was found (ID); the accession number of the viral sample where the match was found (FileWhereFound); the type of organism (Organism); the "bin" size (Bin #) indicating the size of the fragment matched wherein "Bin25" is any fragment from 25-49 base pairs, "Bin50" is any fragment from 50-74 base pairs, and so on; the accession number of the Covid-19 sample providing the matched fragment (CovidID); the number of appearances across the entire 11/18/20 Covid-19 database (App #); the percentage appearance expressed as a decimal (App %); the location of the organism in the GenBank file (AppLoc); the fragment that was matched (Strip); and the location of that fragment relative to MW194121.1.

You will notice that there are some repetitive "nesting doll" types of matches—this is due to the nature of the fragment detection system across each individual sample. All fragments are listed in the drawings, however, and in the computational reduction process, because of overlap, some fragments, depending on the Super Organism used as a starting point, will simply be redundant.

In creation of the vaccine candidate we can also view that vaccine not only as a reductive entity which can be manufactured from a variety of possible starting organisms, but also as a complete organism which has potentially been "neutered" of its destructive features.

In order to arrive at that possibility, we must first find a Covid-19 sample which contains all of these structures. Of the 27,632 complete Covid-19 sequences in the Nov. 18, 2020 Covid-19 database, there are 21,466 which contain all 92 fragments, and 22,895 which contain the maximum of 24 of the 92 of the fragments in non-overlapping configurations.

So to create a reductive vaccine, computationally those fragments are removed to create the vaccine candidate as shown in this patent's sequence file. The original reference sequence and can be downloaded from NIH via the reference MW194121.1. As previously stated, there are also 21,466 other potential reference candidates which could be used as Super Organisms for the next generation of vaccines based on these fragments. That list is available upon request.

This application also seeks to cover the RNA transcript of each of the fragments. It may well be that RNA transcript vaccines based on these fragments would be of equal or greater efficacy in triggering a useful immune response.

It should also be noted that while the majority of these fragments are relatively short (25-49 base pairs) at 25 base pairs, a fragment has only a 1 in 1.12 quadrillion ($4^{25}$) chance of occurring—in the entire history of the planet. In other words, at a 90% recurrence rate across the entire Covid-19 genome, these fragments represent viable mathematical targets for vaccines.

This application identifies 92 such fragments.

SEQUENCE LISTING

```
<160> NUMBER OF SEQ ID NOS: 185

<210> SEQ ID NO 1
<211> LENGTH: 25
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 1
tttttaaacg ggtttgcggt gtaag                                          25

<210> SEQ ID NO 2
<211> LENGTH: 27
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW206032.1.

<400> SEQUENCE: 2
tttttaaacg ggtttgcggt gtaagtg                                        27

<210> SEQ ID NO 3
<211> LENGTH: 25
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW002823.1.

<400> SEQUENCE: 3
aaattacatt acacataaac gaact                                          25

<210> SEQ ID NO 4
<211> LENGTH: 30
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 4
tccctactat aactcaaatg aatcttaagt                                     30
```

```
<210> SEQ ID NO 5
<211> LENGTH: 29
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW202198.1.

<400> SEQUENCE: 5
tccctactat aactcaaatg aatcttaag                                          29

<210> SEQ ID NO 6
<211> LENGTH: 29
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 6
ttcttttcct tgctttcgtg gtattcttg                                          29

<210> SEQ ID NO 7
<211> LENGTH: 30
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT834360.1.

<400> SEQUENCE: 7 cttcttttc ttgctttcgt ggtattcttg                                          30

<210> SEQ ID NO 8
<211> LENGTH: 39
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT806884.1.

<400> SEQUENCE: 8
aaattacatt acacataaac gaacttatgg atttgttta                               39

<210> SEQ ID NO 9
<211> LENGTH: 43
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW190342.1.

<400> SEQUENCE: 9
aaattacatt acacataaac gaacttatgg atttgtttat gag                          43

<210> SEQ ID NO 10
<211> LENGTH: 25
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW227490.1.
```

-continued

```
<400> SEQUENCE: 10
gcccgtctta caccgtgcgg cacag                                          25

<210> SEQ ID NO 11
<211> LENGTH: 26
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW206032.1.

<400> SEQUENCE: 11
ccgtcttaca ccgtgcggca caggca                                         26

<210> SEQ ID NO 12
<211> LENGTH: 30
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT994881.1.

<400> SEQUENCE: 12 ttcttttttct tgctttcgtg gtattcttgc                                    30

<210> SEQ ID NO 13
<211> LENGTH: 31
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW023466.1.

<400> SEQUENCE: 13 ttcttttttct tgctttcgtg gtattcttgc t                                  31

<210> SEQ ID NO 14
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 14
gcccgtctta caccgtgcgg cacaggca                                       28

<210> SEQ ID NO 15
<211> LENGTH: 34
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW166120.1.

<400> SEQUENCE: 15
acttcctcaa ggaacaacat tgccaaaagg cttc                                34

<210> SEQ ID NO 16
<211> LENGTH: 36
<212> TYPE: DNA
```

```
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 16
caacttcctc aaggaacaac attgccaaaa ggcttc                                    36

<210> SEQ ID NO 17
<211> LENGTH: 37
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW185153.1.

<400> SEQUENCE: 17
caacttcctc aaggaacaac attgccaaaa ggcttct                                   37

<210> SEQ ID NO 18
<211> LENGTH: 29
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT627244.1.

<400> SEQUENCE: 18
ctggtaaagg ccaacaacaa caaggccaa                                            29

<210> SEQ ID NO 19
<211> LENGTH: 31
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW208029.1.

<400> SEQUENCE: 19
acaaaacatt cccaccaaca gagcctaaaa a                                         31

<210> SEQ ID NO 20
<211> LENGTH: 25
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW165865.1.

<400> SEQUENCE: 20
gcctatatgg aagagcccta atgtg                                                25

<210> SEQ ID NO 21
<211> LENGTH: 26
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT791883.1.

<400> SEQUENCE: 21
gcctatatgg aagagcccta atgtgt                                               26
```

<210> SEQ ID NO 22
<211> LENGTH: 27
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT419820.1.

<400> SEQUENCE: 22
gcctatatgg aagagcccta atgtgta                                              27

<210> SEQ ID NO 23
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW166144.1.

<400> SEQUENCE: 23
gcctatatgg aagagcccta atgtgtaa                                             28

<210> SEQ ID NO 24
<211> LENGTH: 29
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW000354.1.

<400> SEQUENCE: 24
gcctatatgg aagagcccta atgtgtaaa                                            29

<210> SEQ ID NO 25
<211> LENGTH: 30
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT790522.1.

<400> SEQUENCE: 25
gcctatatgg aagagcccta atgtgtaaaa                                           30

<210> SEQ ID NO 26
<211> LENGTH: 31
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW155545.1.

<400> SEQUENCE: 26
gcctatatgg aagagcccta atgtgtaaaa t                                         31

<210> SEQ ID NO 27
<211> LENGTH: 32
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This fragment was originally scanned from NIH ID: LC571023.1.

<400> SEQUENCE: 27
gcctatatgg aagagcccta atgtgtaaaa tt                    32

<210> SEQ ID NO 28
<211> LENGTH: 33
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This fragment was originally scanned from NIH ID: MW243586.1.

<400> SEQUENCE: 28
gcctatatgg aagagcccta atgtgtaaaa tta 33

<210> SEQ ID NO 29
<211> LENGTH: 35
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MT510690.1.

<400> SEQUENCE: 29
gcctatatgg aagagcccta atgtgtaaaa ttaat 35

<210> SEQ ID NO 30
<211> LENGTH: 36
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MT947556.1.

<400> SEQUENCE: 30
gcctatatgg aagagcccta atgtgtaaaa ttaatt 36

<210> SEQ ID NO 31
<211> LENGTH: 37
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW023460.1.

<400> SEQUENCE: 31
gcctatatgg aagagcccta atgtgtaaaa ttaattt 37

<210> SEQ ID NO 32
<211> LENGTH: 38
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MT886288.1.

<400> SEQUENCE: 32
gcctatatgg aagagcccta atgtgtaaaa ttaatttt 38

<210> SEQ ID NO 33
<211> LENGTH: 39

-continued

```
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW056149.1.

<400> SEQUENCE: 33
gcctatatgg aagagcccta atgtgtaaaa ttaatttta                           39

<210> SEQ ID NO 34
<211> LENGTH: 41
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW067727.1.

<400> SEQUENCE: 34
gcctatatgg aagagcccta atgtgtaaaa ttaattttag t                        41

<210> SEQ ID NO 35
<211> LENGTH: 42
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT820471.1.

<400> SEQUENCE: 35
gcctatatgg aagagcccta atgtgtaaaa ttaattttag ta                       42

<210> SEQ ID NO 36
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW023428.1.

<400> SEQUENCE: 36
cctaatgtgt aaaattaatt ttagtagt                                       28

<210> SEQ ID NO 37
<211> LENGTH: 43
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW056159.1.

<400> SEQUENCE: 37
gcctatatgg aagagcccta atgtgtaaaa ttaattttag tag                      43

<210> SEQ ID NO 38
<211> LENGTH: 34
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT577359.1.

<400> SEQUENCE: 38
```
aagagcccta atgtgtaaaa ttaattttag tagt                                34

<210> SEQ ID NO 39
<211> LENGTH: 35
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT451653.1.

<400> SEQUENCE: 39
gaagagccct aatgtgtaaa attaatttta gtagt                               35

<210> SEQ ID NO 40
<211> LENGTH: 44
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 40
gcctatatgg aagagcccta atgtgtaaaa ttaattttag tagt                     44

<210> SEQ ID NO 41
<211> LENGTH: 45
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT632518.1.

<400> SEQUENCE: 41
tgcctatatg gaagagccct aatgtgtaaa attaatttta gtagt                    45

<210> SEQ ID NO 42
<211> LENGTH: 45
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT990449.1.

<400> SEQUENCE: 42
gcctatatgg aagagcccta atgtgtaaaa ttaattttag tagtg                    45

<210> SEQ ID NO 43
<211> LENGTH: 46
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT970317.1.

<400> SEQUENCE: 43
gcctatatgg aagagcccta atgtgtaaaa ttaattttag tagtgc                   46

<210> SEQ ID NO 44
<211> LENGTH: 47
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This
fragment was originally scanned from NIH ID: MW010251.1.

<400> SEQUENCE: 44
gcctatatgg aagagcccta atgtgtaaaa ttaattttag tagtgct        47

<210> SEQ ID NO 45
<211> LENGTH: 25
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: LR897977.1.

<400> SEQUENCE: 45
tttggcctct tttgtttact caacc 25

<210> SEQ ID NO 46
<211> LENGTH: 26
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MT843306.1.

<400> SEQUENCE: 46
catacaattg ttgtgatgat gattat 26

<210> SEQ ID NO 47
<211> LENGTH: 27
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW208026.1.

<400> SEQUENCE: 47
catacaattg ttgtgatgat gattatt 27

<210> SEQ ID NO 48
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW265603.1.

<400> SEQUENCE: 48
actttattat gattcaatga gttatgag 28

<210> SEQ ID NO 49
<211> LENGTH: 25
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW265603.1.

<400> SEQUENCE: 49
agggcaattc accatttcat cctct 25

<210> SEQ ID NO 50

```
<211> LENGTH: 37
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW020077.1.

<400> SEQUENCE:

-continued tgaaagagcc accacatttt caccg                                        25

<210> SEQ ID NO 56
<211> LENGTH: 27
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW240744.1.

<400> SEQUENCE: 56
tgaaagagcc accacatttt caccgag 27

<210> SEQ ID NO 57
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW205986.1.

<400> SEQUENCE: 57
tgaaagagcc accacatttt caccgagg 28

<210> SEQ ID NO 58
<211> LENGTH: 29
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW221275.1.

<400> SEQUENCE: 58
tgaaagagcc accacatttt caccgaggc 29

<210> SEQ ID NO 59
<211> LENGTH: 30
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MT581414.1.

<400> SEQUENCE: 59
tgaaagagcc accacatttt caccgaggcc 30

<210> SEQ ID NO 60
<211> LENGTH: 31
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MT966110.1.

<400> SEQUENCE: 60
tgaaagagcc accacatttt caccgaggcc a 31

<210> SEQ ID NO 61
<211> LENGTH: 32
<212> TYPE: DNA
<213> ORGANISM: Artificial Sequence
<220> FEATURE:

-continued

<223> OTHER INFORMATION: SEQ ID NOs 1-92 are DNA fragments found in a wide variety of Covid-19 samples (see Specification). This fragment was originally scanned from NIH ID: MW053302.1.

<400> SEQUENCE: 61
tgaaagagcc accacatttt caccgaggcc ac 32

<210> SEQ ID NO 62
<211> LENGTH: 27
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW134158.1.

<400> SEQUENCE: 62
taaacgaact ttaaaatctg tgtggct 27

<210> SEQ ID NO 63
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW190326.1.

<400> SEQUENCE: 63
accacatttt caccgaggcc acgcggag 28

<210> SEQ ID NO 64
<211> LENGTH: 29
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW035533.1.

<400> SEQUENCE: 64
caccacattt tcaccgaggc cacgcggag 29

<210> SEQ ID NO 65
<211> LENGTH: 35
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW206398.1.

<400> SEQUENCE: 65
aagagccacc acattttcac cgaggccacg cggag 35

<210> SEQ ID NO 66
<211> LENGTH: 36
<212> TYPE: DNA
<213> ORGANISM: Artificial Sequence
<220> FEATURE:
<223> OTHER INFORMATION: SEQ ID NOs 1-92 are DNA fragments found in a wide variety of Covid-19 samples (see Specification). This fragment was originally scanned from NIH ID: MW206068.1.

<400> SEQUENCE: 66
aaagagccac cacattttca ccgaggccac gcggag 36

```
<210> SEQ ID NO 67
<211> LENGTH: 33
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW134171.1.

<400> SEQUENCE: 67
tgaaagagcc accacatttt caccgaggcc acg                                    33

<210> SEQ ID NO 68
<211> LENGTH: 37
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT676417.1.

<400> SEQUENCE: 68
tgaaagagcc accacatttt caccgaggcc acgcgga                                37

<210> SEQ ID NO 69
<211> LENGTH: 38
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 69
tgaaagagcc accacatttt caccgaggcc acgcggag                               38

<210> SEQ ID NO 70
<211> LENGTH: 39
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW237708.1.

<400> SEQUENCE: 70
tgaaagagcc accacatttt caccgaggcc acgcggagt                              39

<210> SEQ ID NO 71
<211> LENGTH: 39
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW244016.1.

<400> SEQUENCE: 71
ttgaaagagc caccacattt tcaccgaggc cacgcggag                              39

<210> SEQ ID NO 72
<211> LENGTH: 40
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT997958.1.
```

```
<400> SEQUENCE: 72
tgaaagagcc accacatttt caccgaggcc acgcggagta                    40

<210> SEQ ID NO 73
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 73
ggttttccat ttaataaatg gggtaagg                                 28

<210> SEQ ID NO 74
<211> LENGTH: 27
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1

<400> SEQUENCE: 74
aatgatgaat gtcgcaaaat atactca                                  27

<210> SEQ ID NO 75
<211> LENGTH: 33
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW217345.1.

<400> SEQUENCE: 75
ggtccagaac aaacccaagg aaattttggg gac                           33

<210> SEQ ID NO 76
<211> LENGTH: 26
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT451283.1.

<400> SEQUENCE: 76
gtccacgagt gctttgttaa gcgtgt                                   26

<210> SEQ ID NO 77
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 77
gtccacgagt gctttgttaa gcgtgttg                                 28

<210> SEQ ID NO 78
<211> LENGTH: 26
<212> TYPE: DNA
<213> ORGANISM: Artificial Sequence
```

```
<220> FEATURE:
<223> OTHER INFORMATION: SEQ ID NOs 1-92 are DNA fragments found in a
      wide variety of Covid-19 sam <210> SEQ ID NO 84
<211> LENGTH: 32
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT827832.1.

<400> SEQUENCE: 84
ttctctaaac gaactttaaa atctgtgtgg ct                                32

<210> SEQ ID NO 85
<211> LENGTH: 33
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW023552.1.

<400> SEQUENCE: 85
gttctctaaa cgaactttaa aatctgtgtg gct                               33

<210> SEQ ID NO 86
<211> LENGTH: 32
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT827825.1.

<400> SEQUENCE: 86
tgttctctaa acgaacttta aaatctgtgt gg                                32

<210> SEQ ID NO 87
<211> LENGTH: 34
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 87
tgttctctaa acgaacttta aaatctgtgt ggct                              34

<210> SEQ ID NO 88
<211> LENGTH: 35
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT252754.1.

<400> SEQUENCE: 88
ctgttctcta acgaacttt aaaatctgtg tggct                              35

<210> SEQ ID NO 89
<211> LENGTH: 36
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW012266.1.

<400> SEQUENCE: 89
tctgttctct aaacgaactt taaaatctgt gtggct                                36

<210> SEQ ID NO 90
<211> LENGTH: 37
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MT827839.1.

<400> SEQUENCE: 90
atctgttctc taaacgaact ttaaaatctg tgtggct                               37

<210> SEQ ID NO 91
<211> LENGTH: 28
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: MW265603.1.

<400> SEQUENCE: 91
gtctttattt caccttataa ttcacaga                                         28

<210> SEQ ID NO 92
<211> LENGTH: 27
<212> TYPE: DNA
<213> ORGANISM: Artificial Sequence
<220> FEATURE:
<223> OTHER INFORMATION: SEQ ID NOs 1-92 are DNA fragments found in a
      wide variety of Covid-19 samples (see Specification). This
      fragment was originally scanned from NIH ID: LR897977.1.

<400> SEQUENCE: 92
tctttatttc accttataat tcacaga                                          27

<210> SEQ ID NO 93
<211> LENGTH: 25
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 93
uuuuuaaacg gguuugcggu guaag                                            25

<210> SEQ ID NO 94
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 94
uuuuuaaacg gguuugcggu guaagug                                          27

<210> SEQ ID NO 95
<211> LENGTH: 25
<212> TYPE: RNA
<213> ORGANISM: Artificial Sequence
<220> FEATURE:

<223> OTHER INFORMATION: SEQ ID NOs 93-184 are the mRNA transcriptions
      of SEQ ID NOs 1-92.

<400> SEQUENCE: 95
aaauuacauu acacauaaac gaacu                                          25

<210> SEQ ID NO 96
<211> LENGTH: 30
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 96
ucccuacuau aacucaaaug aaucuuaagu                                     30

<210> SEQ ID NO 97
<211> LENGTH: 29
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 97
ucccuacuau aacucaaaug aaucuuaag                                      29

<210> SEQ ID NO 98
<211> LENGTH: 29
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 98
uucuuuuucu ugcuuucgug guauucuug                                      29

<210> SEQ ID NO 99
<211> LENGTH: 30
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 99
cuucuuuuuc uugcuuucgu gguauucuug                                     30

<210> SEQ ID NO 100
<211> LENGTH: 39
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 100
aaauuacauu acacauaaac gaacuuaugg auuuguuua                           39

<210> SEQ ID NO 101
<211> LENGTH: 43
<212> TYPE: RNA
<213> ORGANISM: Artificial Sequence
<220> FEATURE:
<223> OTHER INFORMATION: SEQ ID NOs 93-184 are the mRNA transcriptions of SEQ ID NOs 1-92.

<400> SEQUENCE: 101
aaauuacauu acacauaaac gaacuuaugg auuuguuuau gag             43

<210> SEQ ID NO 102
<211> LENGTH: 25
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 102
gcccgucuua caccgugcgg cacag                                 25

<210> SEQ ID NO 103
<211> LENGTH: 26
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 103
ccgucuuaca ccgugcggca caggca                                26

<210> SEQ ID NO 104
<211> LENGTH: 30
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 104
uucuuuuucu ugcuuucgug guauucuugc                            30

<210> SEQ ID NO 105
<211> LENGTH: 31
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 105
uucuuuuucu ugcuuucgug guauucuugc u                          31

<210> SEQ ID NO 106
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 106
gcccgucuua caccgugcgg cacaggca                              28

<210> SEQ ID NO 107
<211> LENGTH: 34
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

```
<400> SEQUENCE: 107
acuuccucaa ggaacaacau ugccaaaagg cuuc                              34

<210> SEQ ID NO 108
<211> LENGTH: 36
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 108
caacuuccuc aaggaacaac auugccaaaa ggcuuc                            36

<210> SEQ ID NO 109
<211> LENGTH: 37
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 109
caacuuccuc aaggaacaac auugccaaaa ggcuucu                           37

<210> SEQ ID NO 110
<211> LENGTH: 29
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 110
cugguaaagg ccaacaacaa caaggccaa                                    29

<210> SEQ ID NO 111
<211> LENGTH: 31
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 111
acaaaacauu cccaccaaca gagccuaaaa a                                 31

<210> SEQ ID NO 112
<211> LENGTH: 25
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 112
gccuauaugg aagagcccua augug                                        25

<210> SEQ ID NO 113
<211> LENGTH: 26
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.
```

```
<400> SEQUENCE: 113
gccuauaugg aagagcccua augugu                                              26

<210> SEQ ID NO 114
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 114
gccuauaugg aagagcccua augugua                                             27

<210> SEQ ID NO 115
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 115
gccuauaugg aagagcccua auguguaa                                            28

<210> SEQ ID NO 116
<211> LENGTH: 29
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 116
gccuauaugg aagagcccua auguguaaa                                           29

<210> SEQ ID NO 117
<211> LENGTH: 30
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 117
gccuauaugg aagagcccua auguguaaaa                                          30

<210> SEQ ID NO 118
<211> LENGTH: 31
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 118
gccuauaugg aagagcccua auguguaaaa u                                        31

<210> SEQ ID NO 119
<211> LENGTH: 32
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 119
```
gccuauaugg aagagcccua auguguaaaa uu                                    32

<210> SEQ ID NO 120
<211> LENGTH: 33
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 120
gccuauaugg aagagcccua auguguaaaa uua                                   33

<210> SEQ ID NO 121
<211> LENGTH: 35
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 121
gccuauaugg aagagcccua auguguaaaa uuaau                                 35

<210> SEQ ID NO 122
<211> LENGTH: 36
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 122
gccuauaugg aagagcccua auguguaaaa uuaauu                                36

<210> SEQ ID NO 123
<211> LENGTH: 37
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 123
gccuauaugg aagagcccua auguguaaaa uuaauuu                               37

<210> SEQ ID NO 124
<211> LENGTH: 38
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 124
gccuauaugg aagagcccua auguguaaaa uuaauuuu                              38

<210> SEQ ID NO 125
<211> LENGTH: 39
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 125

```
gccuauaugg aagagcccua auguguaaaa uuaauuuua                    39
```

<210> SEQ ID NO 126
<211> LENGTH: 41
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 126

```
gccuauaugg aagagcccua auguguaaaa uuaauuuuag u                 41
```

<210> SEQ ID NO 127
<211> LENGTH: 42
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 127

```
gccuauaugg aagagcccua auguguaaaa uuaauuuuag ua                42
```

<210> SEQ ID NO 128
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 128

```
ccuaaugugu aaaauuaauu uuaguagu                                28
```

<210> SEQ ID NO 129
<211> LENGTH: 43
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 129

```
gccuauaugg aagagcccua auguguaaaa uuaauuuuag uag               43
```

<210> SEQ ID NO 130
<211> LENGTH: 34
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 130

```
aagagcccua auguguaaaa uuaauuuuag uagu                         34
```

<210> SEQ ID NO 131
<211> LENGTH: 35
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 131

```
gaagagcccu aauguguaaa auuaauuuua guagu                        35
```

<210> SEQ ID NO 132
<211> LENGTH: 44
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 132
gccuauaugg aagagcccua auguguaaaa uuaauuuuag uagu                    44

<210> SEQ ID NO 133
<211> LENGTH: 45
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 133
ugccuauaug gaagagcccu aauguguaaa auuaauuuua guagu                   45

<210> SEQ ID NO 134
<211> LENGTH: 45
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 134
gccuauaugg aagagcccua auguguaaaa uuaauuuuag uagug                   45

<210> SEQ ID NO 135
<211> LENGTH: 46
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 135
gccuauaugg aagagcccua auguguaaaa uuaauuuuag uagugc                  46

<210> SEQ ID NO 136
<211> LENGTH: 47
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 136
gccuauaugg aagagcccua auguguaaaa uuaauuuuag uagugcu                 47

<210> SEQ ID NO 137
<211> LENGTH: 25
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 137
uuuggccucu uuuguuuacu caacc                                         25

<210> SEQ ID NO 138
<211> LENGTH: 26
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 138
cauacaauug uugugaugau gauuau                                          26

<210> SEQ ID NO 139
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 139
cauacaauug uugugaugau gauuauu                                         27

<210> SEQ ID NO 140
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 140
acuuuauuau gauucaauga guuaugag                                        28

<210> SEQ ID NO 141
<211> LENGTH: 25
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 141
agggcaauuc accauuucau ccucu                                           25

<210> SEQ ID NO 142
<211> LENGTH: 37
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 142
guguuuugau aaauucaaag ugaauucaac auuagaa                              37

<210> SEQ ID NO 143
<211> LENGTH: 41
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 143
uagaguguuu ugauaaauuc aaagugaauu caacauuaga a                         41

```
<210> SEQ ID NO 144
<211> LENGTH: 31
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 144
agaaguagug gaaaauccua ccauacagaa a                                    31

<210> SEQ ID NO 145
<211> LENGTH: 32
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 145
agaaguagug gaaaauccua ccauacagaa ag                                   32

<210> SEQ ID NO 146
<211> LENGTH: 26
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 146
ucaucuaaac gaacaaacua aaaugu                                          26

<210> SEQ ID NO 147
<211> LENGTH: 25
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 147
ugaaagagcc accacauuuu caccg                                           25

<210> SEQ ID NO 148
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 148
ugaaagagcc accacauuuu caccgag                                         27

<210> SEQ ID NO 149
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 149
ugaaagagcc accacauuuu caccgagg                                        28

<210> SEQ ID NO 150
```

```
<211> LENGTH: 29
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 150
ugaaagagcc accacauuuu caccgaggc                                           29

<210> SEQ ID NO 151
<211> LENGTH: 30
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 151
ugaaagagcc accacauuuu caccgaggcc                                          30

<210> SEQ ID NO 152
<211> LENGTH: 31
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 152
ugaaagagcc accacauuuu caccgaggcc a                                        31

<210> SEQ ID NO 153
<211> LENGTH: 32
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 153
ugaaagagcc accacauuuu caccgaggcc ac                                       32

<210> SEQ ID NO 154
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 154
uaaacgaacu uuaaaaucug uguggcu                                             27

<210> SEQ ID NO 155
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 155
accacauuuu caccgaggcc acgcggag                                            28

<210> SEQ ID NO 156
<211> LENGTH: 29
```

```
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 156
caccacauuu ucaccgaggc cacgcggag                                        29

<210> SEQ ID NO 157
<211> LENGTH: 35
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 157
aagagccacc acauuuucac cgaggccacg cggag                                 35

<210> SEQ ID NO 158
<211> LENGTH: 36
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 158
aaagagccac cacauuuuca ccgaggccac gcggag                                36

<210> SEQ ID NO 159
<211> LENGTH: 33
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 159
ugaaagagcc accacauuuu caccgaggcc acg                                   33

<210> SEQ ID NO 160
<211> LENGTH: 37
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 160
ugaaagagcc accacauuuu caccgaggcc acgcgga                               37

<210> SEQ ID NO 161
<211> LENGTH: 38
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 161
ugaaagagcc accacauuuu caccgaggcc acgcggag                              38

<210> SEQ ID NO 162
<211> LENGTH: 39
<212> TYPE: RNA
```

<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 162
ugaaagagcc accacauuuu caccgaggcc acgcggagu                              39

<210> SEQ ID NO 163
<211> LENGTH: 39
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 163
uugaaagagc caccacauuu ucaccgaggc cacgcggag                              39

<210> SEQ ID NO 164
<211> LENGTH: 40
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 164
ugaaagagcc accacauuuu caccgaggcc acgcggagua                             40

<210> SEQ ID NO 165
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 165
gguuuuccau uuaauaaaug ggguaagg                                          28

<210> SEQ ID NO 166
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 166
aaugaugaau gucgcaaaau auacuca                                           27

<210> SEQ ID NO 167
<211> LENGTH: 33
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 167
gguccagaac aaacccaagg aaauuuggg gac                                     33

<210> SEQ ID NO 168
<211> LENGTH: 26
<212> TYPE: RNA
<213> ORGANISM: Artificial Sequence

```
<220> FEATURE:
<223> OTHER INFORMATION: SEQ ID NOs 93-184 are the mRNA transcriptions
      of SEQ ID NOs 1-92.

<400> SEQUENCE: 168
guccacgagu gcuuguuaa gcgugu                                             26

<210> SEQ ID NO 169
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 169
guccacgagu gcuuguuaa gcguguug                                           28

<210> SEQ ID NO 170
<211> LENGTH: 26
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 170
ugccacaaga gcacuauguu agaauu                                            26

<210> SEQ ID NO 171
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 171
gugccacaag agcacuaugu uagaauu                                           27

<210> SEQ ID NO 172
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 172
cuaaacgaac uuuaaaaucu guguggcu                                          28

<210> SEQ ID NO 173
<211> LENGTH: 29
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 173
ucuaaacgaa cuuuaaaauc uguguggcu                                         29

<210> SEQ ID NO 174
<211> LENGTH: 30
<212> TYPE: RNA
<213> ORGANISM: Artificial Sequence
<220> FEATURE:
```

```
<223> OTHER INFORMATION: SEQ ID NOs 93-184 are the mRNA transcriptions
      of SEQ ID NOs 1-92.

<400> SEQUENCE: 174
cucuaaacga acuuuaaaau cuguguggcu                                            30

<210> SEQ ID NO 175
<211> LENGTH: 31
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 175
ucucuaaacg aacuuuaaaa ucguguggc u                                           31

<210> SEQ ID NO 176
<211> LENGTH: 32
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 176
uucucuaaac gaacuuuaaa aucgugugg cu                                          32

<210> SEQ ID NO 177
<211> LENGTH: 33
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 177
guucucuaaa cgaacuuuaa aaucgugug gcu                                         33

<210> SEQ ID NO 178
<211> LENGTH: 32
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 178
uguucucuaa acgaacuuua aaaucgugu gg                                          32

<210> SEQ ID NO 179
<211> LENGTH: 34
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 179
uguucucuaa acgaacuuua aaaucgugu ggcu                                        34

<210> SEQ ID NO 180
<211> LENGTH: 35
<212> TYPE: RNA
<213> ORGANISM: Artificial Sequence
<220> FEATURE:
<223> OTHER INFORMATION: SEQ ID NOs 93-184 are the mRNA transcriptions
``` of SEQ ID NOs 1-92.

<400> SEQUENCE: 180
cuguucucua aacgaacuuu aaaaucugug uggcu                               35

<210> SEQ ID NO 181
<211> LENGTH: 36
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 181
ucuguucucu aaacgaacuu uaaaaucugu guggcu                              36

<210> SEQ ID NO 182
<211> LENGTH: 37
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 182
aucuguucuc uaaacgaacu uuaaaaucug uguggcu                             37

<210> SEQ ID NO 183
<211> LENGTH: 28
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 183
gucuuuauuu caccuuauaa uucacaga                                       28

<210> SEQ ID NO 184
<211> LENGTH: 27
<212> TYPE: RNA
<213> ORGANISM: Artificial Sequence
<220> FEATURE:
<223> OTHER INFORMATION: SEQ ID NOs 93-184 are the mRNA transcriptions
      of SEQ ID NOs 1-92.

<400> SEQUENCE: 184
ucuuuauuuc accuuauaau ucacaga                                        27

<210> SEQ ID NO 185
<211> LENGTH: 29254
<212> TYPE: DNA
<213> ORGANISM: Artificial Sequence
<220> FEATURE:
<223> OTHER INFORMATION: Based on MW194121.1 as a computational
      reduction vaccine (see Specification for details). This sequence
      is identical to that filed with the original patent.

<400> SEQUENCE: 185
attaaaggtt tataccttcc caggtaacaa accaaccaac tttcgatctc ttgtagatct     60
gttctcgtca ctcggctgca tgcttagtgc actcacgcag tataattaat aactaattac   120
tgtcgttgac aggacacgag taactcgtct atcttctgca ggctgcttac ggtttcgtcc   180
gtgttgcagc cgatcatcag cacatctagg ttttgtccgg gtgtgaccga aaggtaagat   240
ggagagcctt gtccctggtt tcaacgagaa aacacacgtc caacttagtt tgcctgtttt   300

```
acaggttcgc gacgtgctcg tacgtggctt tggagactcc gtggaggagg tcttatcaga      360
ggcacgtcaa catcttaaag atggcacttg tggcttagta gaagttgaaa aaggcgtttt      420
gcctcaactt gaacagccct atgtgttcat caaacgttcg gatgctcgaa ctgcacctca      480
tggtcatgtt atggttgagc tggtagcaga acttgaaggc attcagtacg gtcgtagtgg      540
tgagacactt ggtgtccttg tccctcatgt gggcgaaata ccagtggctt accgcaaggt      600
tcttcttcgt aagaacggta ataaaggagc tggtggccat agttacggcg ccgatctaaa      660
gtcatttgac ttaggcgacg agcttggcac tgatccttat gaagattttc aagaaaactg      720
gaacactaaa catagcagtg gtgttacccg tgaactcatg cgtgagctta cggaggggc       780 atacactcgc tatgtcgata caacttctg tggccctgat ggctacccte ttgagtgcat       840 taaagacctt ctagcacgtg ctggtaaagc ttcatgcact ttgtccgaac aactggactt      900
tattgacact aagagggggtg tatactgctg ccgtgaacat gagcatgaaa ttgcttggta    960
cacggaacgt tctgaaaaga gctatgaatt gcagacacct tttgaaatta aattggcaaa     1020
gaaatttgac accttcaatg gggaatgtcc aaattttgta tttcccttaa attccataat     1080
caagactatt caaccaaggg ttgaaaagaa aaagcttgat ggctttatgg gtagaattcg     1140
atctgtctat ccagttgcgt caccaaatga atgcaaccaa atgtgccttt caactctcat     1200
gaagtgtgat cattgtggtg aaacttcatg gcagacgggc gattttgtta aagccacttg     1260
cgaattttgt ggcactgaga atttgactaa agaaggtgcc actacttgtg gttacttacc     1320
ccaaaatgct gttgttaaaa tttattgtcc agcatgtcac aattcagaag taggacctga     1380
gcatagtctt gccgaatacc ataatgaatc tggcttgaaa accattcttc gtaagggtgg     1440
tcgcactatt gccttttggag gctgtgtgtt ctcttatgtt ggttgccata caagtgtgc      1500 ttattgggtt ccacgtgcta gcgctaacat aggttgtaac catacaggtg ttgttggaga     1560
aggttccgaa ggtctcaatg acaaccttct tgaaatactc caaaaagaga agtcaacat      1620 caatattgtt ggtgacttta acttaatga agagatcgcc attattttgg catctttttc      1680
tgcttccaca agtgcttttg tggaaactgt gaaaggtttg gattataaag cattcaaaca     1740
aattgttgaa tcctgtggta attttaaagt tacaaaagga aaagctaaaa aaggtgcctg     1800
gaatattggt gaacagaaat caatactgag tcctctttat gcatttgcat cagaggctgc     1860
tcgtgttgta cgatcaattt tctcccgcac tcttgaaact gctcaaaatt ctgtgcgtgt     1920
tttacagaag gccgctataa caatactaga tggaatttca cagtattcac tgagactcat     1980
tgatgctatg atgttcacat ctgatttggc tactaacaat ctagttgtaa tggcctacat     2040
tacaggtggt gttgttcagt tgacttcgca gtggctaact aacatctttg cactgtttta     2100
tgaaaaactc aaaccgtcc ttgattggct tgaagagaaa tttaaggaag gtgtagagtt      2160
tcttagagac ggttgggaaa ttgttaaatt tatctcaacc tgtgcttgtg aaattgtcgg     2220
tggacaaatt gtcacctgtg caaggaaat taaggagagt gttcagacat ctttaagct       2280 tgtaaataaa ttttttggctt tgtgtgctga ctctatcatt attggtggag ctaaacttaa    2340
agccttgaat ttaggtgaaa catttgtcac gcactcaaag ggattgtaca gaaagtgtgt     2400
taaatccaga gaagaaactg gcctactcat gcctctaaaa gccccaaaag aaattatctt     2460
cttagaggga gaaacacttc ccacagaagt gttaacagag gaagttgtct tgaaaactgg     2520
tgatttacaa ccattagaac aacctactag tgaagctgtt gaagctccat tggttggtac     2580 accagttgt attaacgggc ttatgttgct cgaaatcaaa gacacagaaa agtactgtgc      2640
```

-continued

```
ccttgcacct aatatgatgg taacaaacaa taccttcaca ctcaaaggcg gtgcaccaac    2700
aaaggttact tttggtgatg acactgtgat agaagtgcaa ggttacaaga gtgtgaatat    2760
cacttttgaa cttgatgaaa ggattgataa agtacttaat gagaagtgtt ctgcctatac    2820
agttgaactc ggtacagaag taaatgagtt cgcctgtgtt gtggcagatg ctgtcataaa    2880
aactttgcaa ccagtatctg aattacttac accactgggc attgatttag atgagtggag    2940
tatggctaca tactacttat ttgatgagtc tggtgagttt aaattggctt cacatatgta    3000
ttgttctttt tacccticcag atgaggatga agaagaaggt gattgtgaag aagaagagtt    3060
tgagccatca actcaatatg agtatggtac tgaagatgat taccaaggta aacctttgga    3120
atttggtgcc acttctgctg ctcttcaacc tgaagaagag caagaagaag attggttaga    3180
tgatgatagt caacaaactg ttggtcaaca agacggcagt gaggacaatc agacaactac    3240
tattcaaaca attgttgagg ttcaacctca attagagatg gaacttacac cagttgttca    3300
gactattgaa gtgaatagtt ttagtggtta ttttaaaactt actgacaatg tatacattaa    3360 aaaatgcagac attgtggaag aagctaaaaa ggtaaaacca acagtggttg ttaatgcagc    3420
caatgtttac cttaaacatg gaggaggtgt tgcaggagcc ttaaataagg ctactaacaa    3480
tgccatgcaa gttgaatctg atgattacat agctactaat ggaccactta agtgggtgg    3540 tagttgtgtt ttaagcggac acaatcttgc taaacactgt cttcatgttg tcggcccaaa    3600
tgttaacaaa ggtgaagaca ttcaacttct taagagtgct tatgaaaatt ttaatcagca    3660
cgaagttcta cttgcaccat tattatcagc tggtattttt ggtgctgacc ctatacattc    3720
tttaagagtt tgtgtagata ctgttcgcac aaatgtctac ttagctgtct ttgataaaaa    3780
tctctatgac aaacttgttt caagcttttt ggaaatgaag agtgaaaagc aagttgaaca    3840
aaagatcgct gagattccta agaggaagt taagccattt ataactgaaa gtaaaccttc    3900
agttgaacag agaaaacaag atgataagaa aatcaaagct tgtgttgaag aagttacaac    3960
aactctggaa gaaactaagt tcctcacaga aaacttgtta cttatatttg acattaatgg    4020
caatcttcat ccagattctg ccactcttgt tagtgacatt gacatcactt tcttaaagaa    4080
agatgctcca tatatagtgg gtgatgttgt tcaagagggt gttttaactg ctgtggttat    4140
acctactaaa aaggctggtg gcactactga aatgctagcg aaagctttga gaaaagtgcc    4200
aacagacaat tatataacca cttacccggg tcagggttta aatggttaca ctgtagagga    4260
ggcaaagaca gtgcttaaaa agtgtaaaag tgccttttac attctaccat ctattatctc    4320
taatgagaag caagaaattc ttggaactgt ttcttggaat ttgcgagaaa tgcttgcaca    4380
tgcagaagaa acacgcaaat taatgcctgt ctgtgtggaa actaaagcca tagtttcaac    4440
tatacagcgt aaatataagg gtattaaaat acaagagggt gtagttgatt atggtgctag    4500
attttacttt tacaccagta aaacaactgt agcgtcactt atcaacacac ttaacgatct    4560
aaatgaaact cttgttacaa tgccacttgg ctatgtaaca catggcttaa atttggaaga    4620
agctgctcgg tatatgagat ctctcaaagt gccagctaca gtttctgttt cttcacctga    4680
tgctgttaca gcgtataatg gttatcttac ttcttcttct aaaacacctg aagaacattt    4740
tattgaaacc atctcacttg ctggttccta taaagattgg tcctattctg acaatctac    4800 acaactaggt atagaatttc ttaagagagg tgataaaagt gtatattaca ctagtaatcc    4860
taccacattc cacctagatg gtgaagttat caccttttgac aatcttaaga cacttctttc    4920
tttgagagaa gtgaggacta ttaaggtgtt tacaacagta gacaacatta acctccacac    4980
gcaagttgtg gacatgtcaa tgacatatgg acaacagttt ggtccaactt atttggatgg    5040
```

```
agctgatgtt actaaaataa aacctcataa ttcacatgaa ggtaaaacat tttatgtttt    5100
acctaatgat gacactctac gtgttgaggc ttttgagtac taccacacaa ctgatcctag    5160
ttttctgggt aggtacatgt cagcattaaa tcacactaaa aagtggaaat acccacaagt    5220
taatggttta acttctatta aatgggcaga taacaactgt tatcttgcca ctgcattgtt    5280
aacactccaa caaatagagt tgaagtttaa tccacctgct ctacaagatg cttattacag    5340
agcaagggct ggtgaagctg ctaacttttg tgcacttatc ttagcctact gtaataagac    5400
agtaggtgag ttaggtgatg ttagagaaac aatgagttac ttgtttcaac atgccaattt    5460
agattcttgc aaaagagtct tgaacgtggt gtgtaaaact tgtggacaac agcagacaac    5520
ccttaagggt gtagaagctg ttatgtacat gggcacactt tcttatgaac aatttaagaa    5580
aggtgttcag atacctttgta cgtgtggtaa acaagctaca aaatatctag tacaacagga    5640
gtcacctttt gttatgatgt cagcaccacc tgctcagtat gaacttaagc atggtacatt    5700
tacttgtgct agtgagtaca ctggtaatta ccagtgtggt cactataaac atataacttc    5760
taaagaaact ttgtattgca tagacggtgc tttacttaca aagtcctcag aatacaaagg    5820
tcctattacg gatgttttct acaaagaaaa cagttacaca acaaccataa aaccagttac    5880
ttataaattg gatggtgttg tttgtacaga aattgacccc aagttggaca attattataa    5940
gaaagacaat tcttatttca cagagcaacc aattgatctt gtaccaaacc aaccatatcc    6000
aaacgcaagc ttcgataatt ttaagtttgt atgtgataat atcaaatttg ctgatgattt    6060
aaaccagtta actggttata agaaacctgc ttcaagagag cttaaagtta cattttccc    6120
tgacttaaat ggtgatgtgg tggctattga ttataaacac tacacaccct cttttaagaa    6180
aggagctaaa ttgttacata aacctattgt ttggcatgtt aacaatgcaa ctaataaagc    6240
cacgtataaa ccaaataccc ggtgtatacg ttgtctttgg agcacaaaac cagttgaaac    6300
atcaaattcg tttgatgtac tgaagtcaga ggacgcgcag ggaatggata atcttgcctg    6360
cgaagatcta aaaccagtct ctgagacgtt cttgagtgta atgtgaaaac taccgaagtt    6420
gtaggagaca ttatacttaa accagcaaat aatagtttaa aaattacaga agaggttggc    6480
cacacagatc taatggctgc ttatgtagac aattctagtc ttactattaa gaaacctaat    6540
gaattatcta gagtattagg tttgaaaacc cttgctactc atggtttagc tgctgttaat    6600
agtgtccctt gggatactat agctaattat gctaagcctt tcttaacaa agttgttagt    6660
acaactacta acatagttac acggtgttta aaccgtgttt gtactaatta tatgccttat    6720
ttctttactt tattgctaca attgtgtact tttactagaa gtacaaattc tagaattaaa    6780
gcatctatgc cgactactat agcaaagaat actgttaaga gtgtcggtaa attttgtcta    6840
gaggcttcat ttaattattt gaagtcacct aattttttcta aactgataaa tattataatt    6900
tggttttttac tattaagtgt ttgcctaggt tctttaatct actcaaccgc tgctttaggt    6960
gttttaatgt ctaatttagg catgccttct tactgtactg ttacagaga aggctatttg    7020
aactctacta atgtcactat tgcaacctac tgtactggtt ctataccttg tagtgtttgt    7080
cttagtggtt tagattcttt agacacctat ccttctttag aaactataca aattaccatt    7140
tcatctttta aatgggattt aactgctttt ggcttagttg cagagtggtt tttggcatat    7200
attctttttca ctaggttttt ctatgtactt ggattggctg caatcatgca attgttttcc   7260
agctattttg cagtacattt tattagtaat tcttggctta tgtggttaat aattaatctt   7320
gtacaaatgg ccccgatttc agctatggtt agaatgtaca tcttctttgc atcattttat   7380
```

-continued

```
tatgtatgga aaagttatgt gcatgttgta gacggttgta attcatcaac ttgtatgatg    7440
tgttacaaac gtaatagagc aacaagagtc gaatgtacaa ctattgttaa tggtgttaga    7500
aggtcctttt atgtctatgc taatggaggt aaaggctttt gcaaactaca caattggaat    7560
tgtgttaatt gtgatacatt ctgtgctggt agtacattta ttagtgatga agttgcgaga    7620
gacttgtcac tacagtttaa aagaccaata aatcctactg accagtcttc ttacatcgtt    7680
gatagtgtta cagtgaagaa tggttccatc catctttact ttgataaagc tggtcaaaag    7740
acttatgaaa gacattctct ctctcatttt gttaacttag acaacctgag agctaataac    7800
actaaaggtt cattgcctat taatgttata gttttttgatg gtaaatcaaa atgtgaagaa    7860
tcatctgcaa aatcagcgtc tgtttactac agtcagctta tgtgtcaacc tatactgtta    7920
ctagatcagg cattagtgtc tgatgttggt gatagtgcgg aagttgcagt taaaatgttt    7980
gatgcttacg ttaatacgtt ttcatcaact tttaacgtac caatggaaaa actcaaaaca    8040
ctagttgcaa ctgcagaagc tgaacttgca aagaatgtgt ccttagacaa tgtcttatct    8100
acttttattt cagcagctcg gcaagggttt gttgattcag atgtagaaac taaagatgtt    8160
gttgaatgtc ttaaattgtc acatcaatct gacatagaag ttactggcga tagttgtaat    8220
aactatatgc tcacctataa caaagttgaa aacatgacac cccgtgacct tggtgcttgt    8280
attgactgta gtgcgcgtca tattaatgcg caggtagcaa aaagtcacaa cattgctttg    8340
atatggaacg ttaaagattt catgtcattg tctgaacaac tacgaaaaca aatacgtagt    8400
gctgctaaaa agaataactt accttttaag ttgacatgtg caactactag acaagttgtt    8460
aatgttgtaa caacaaagat agcacttaag ggtggtaaaa ttgttaataa ttggttgaag    8520
cagttaatta aagttacact tgtgttcctt tttgttgctg ctattttcta tttaataaca    8580
cctgttcatg tcatgtctaa acatactgac ttttcaagtg aaatcatagg atacaaggct    8640
attgatggtg gtgtcactcg tgacatagca tctacagata cttgttttgc taacaaacat    8700
gctgattttg acacatggtt tagccagcgt ggtggtagtt atactaatga caaagcttgc    8760
ccattgattg ctgcagtcat aacaagagaa gtgggttttg tcgtgcctgg tttgcctggc    8820
acgatattac gcacaactaa tggtgatttt ttgcatttct tacctagagt ttttagtgca    8880
gttggtaaca tctgttacac accatcaaaa cttatagagt acactgactt tgcaacatca    8940
gcttgtgttt tggctgctga atgtacaatt tttaaagatg cttctggtaa gccagtacca    9000
tattgttatg ataccaatgt actagaaggt tctgttgctt atgaaagttt acgccctgac    9060
acacgttatg tgctcatgga tggctctatt attcaatttc ctaacaccta ccttgaaggt    9120
tctgttagag tggtaacaac ttttgattct gagtactgta ggcacggcac ttgtgaaaga    9180
tcagaagctg gtgtttgtgt atctactagt ggtagatggg tacttaacaa tgattattac    9240
agatctttac caggagtttt ctgtggtgta gatgctgtaa atttacttac taatatgttt    9300
acaccactaa ttcaacctat tggtgctttg gacatatcag catctatagt agctggtggt    9360
attgtagcta tcgtagtaac atgccttgcc tactattta tgaggtttag aagagctttt    9420
ggtgaataca gtcatgtagt tgcctttaat actttactat tccttatgtc attcactgta    9480
ctctgtttaa caccagtttta ctcattctta cctggtgttt attctgttat ttacttgtac    9540
ttgacatttt atcttactaa tgatgtttct ttttagcac atattcagtg gatggttatg    9600
ttcacacctt tagtaccttt ctggataaca attgcttata tcatttgtat ttccacaaag    9660
catttctatt ggttctttag taattaccta aagagacgtg tagtctttaa tggtgtttcc    9720
tttagtactt ttgaagaagc tgcgctgtgc acctttttgt taaataaaga aatgtatcta    9780
```

```
aagttgcgta gtgatgtgct attacctctt acgcaatata atagatactt agctctttat   9840
aataagtaca agtattttag tggagcaatg gatacaacta gctacagaga agctgcttgt   9900
tgtcatctcg caaaggctct caatgacttc agtaactcag gttctgatgt tctttaccaa   9960
ccaccacaaa cctctatcac ctcagctgtt ttgcagagtg gttttagaaa aatggcattc  10020
ccatctggta aagttgaggg ttgtatggta caagtaactt gtggtacaac tacacttaac  10080
ggtctttggc ttgatgacgt agtttactgt ccaagacatg tgatctgcac ctctgaagac  10140
atgcttaacc ctaattatga agatttactc attcgtaagt ctaatcataa tttcttggta  10200
caggctggta atgttcaact cagggttatt ggacattcta tgcaaaattg tgtacttaag  10260
cttaaggttg atacagccaa tcctaagaca cctaagtata agtttgttcg cattcaacca  10320
ggacagactt tttcagtgtt agcttgttac aatggttcac catctggtgt ttaccaatgt  10380
gctatgaggc ccaatttcac tattaagggt tcattcctta atggttcatg tggtagtgtt  10440
ggttttaaca tagattatga ctgtgtctct ttttgttaca tgcaccatat ggaattacca  10500
actggagttc atgctggcac agacttagaa ggtaactttt atggacccttt tgttgacagg  10560
caaacagcac aagcagctgg tacgacaca actattacag ttaatgtttt agcttggttg  10620
tacgctgctg ttataaatgg agacaggtgg tttctcaatc gatttaccac aactcttaat  10680
gactttaacc ttgtggctat gaagtacaat tatgaacctc taacacaaga ccatgttgac  10740
atactaggac ctctttctgc tcaaactgga attgccgttt tagatatgtg tgcttcatta  10800
aaagaattac tgcaaaatgg tatgaatgga cgtaccatat gggtagtgc tttattagaa  10860
gatgaattta cacctttga tgttgttaga caatgctcag gtgttacttt ccaaagtgca  10920
gtgaaaagaa caatcaaggg tacacaccac tggttgttac tcacaatttt gacttcactt  10980
ttagttttag tccagagtac tcaatggtct ttgttctttt ttttgtatga aaatgccttt  11040
ttacctttttg ctatgggtat tattgctatg tctgcttttg caatgatgtt tgtcaaacat  11100
aagcatgcat ttctctgttt gttttttgtta ccttctcttg ccactgtagc ttatttaat  11160
atggtctata tgcctgctag ttgggtgatg cgtattatga catggttgga tatggttgat  11220
actagtttgt ctggttttaa gctaaaagac tgtgttatgt atgcatcagc tgtagtgtta  11280
ctaatcctta tgacagcaag aactgtgtat gatgatggtg ctaggagagt gtggacactt  11340
atgaatgtct tgacactcgt ttataaagtt tattatggta atgctttaga tcaagccatt  11400
tccatgtggg ctcttataat ctctgttact tctaactact caggtgtagt tacaactgtc  11460
atgttttttgg ccagaggtat tgttttatg tgtgttgagt attgccctat tttcttcata  11520
actggtaata cacttcagtg tataatgcta gtttattgtt tcttaggcta ttttttgtact  11580
tgttacgcta ctttagactg actcttggtg tttatgatta cttagtttct acacaggagt  11640
ttagatatat gaattcacag ggactactcc cacccaagaa tagcatagat gccttcaaac  11700
tcaacattaa attgttgggt gttggtggca aaccttgtat caaagtagcc actgtacagt  11760
ctaaaatgtc agatgtaaag tgcacatcag tagtcttact ctcagttttg caacaactca  11820
gagtagaatc atcatctaaa ttgtgggctc aatgtgtcca gttacacaat gacattctct  11880
tagctaaaga tactactgaa gcctttgaaa aatggtttc actacttttct gttttgcttt  11940
ccatgcaggg tgctgtagac ataaacaagc tttgtgaaga aatgctggac aacagggcaa  12000
ccttacaagc tatagcctca gagtttagtt cccttccatc atatgcagct tttgctactg  12060
ctcaagaagc ttatgagcag gctgttgcta atggtgattc tgaagttgtt cttaaaaagt  12120
```

```
tgaagaagtc tttgaatgtg gctaaatctg aatttgaccg tgatgcagcc atgcaacgta    12180
agttggaaaa gatggctgat caagctatga cccaaatgta taaacaggct agatctgagg    12240
acaagagggc aaaagttact agtgctatgc agacaatgct tttcactatg cttagaaagt    12300
tggataatga tgcactcaac aacattatca acaatgcaag agatggttgt gttcccttga    12360
acataatacc tcttacaaca gcagccaaac taatggttgt cataccagac tataacacat    12420
ataaaaatac gtgtgatggt acaacattta cttatgcatc agcattgtgg gaaatccaac    12480
aggttgtaga tgcagatagt aaaattgttc aacttagtga aattagtatg gacaattcac    12540
ctaatttagc atggcctctt attgtaacag ctttaagggc caattctgct gtcaaattac    12600
agaataatga gcttagtcct gttgcactac gacagatgtc ttgtgctgcc ggtactacac    12660
aaactgcttg cactgatgac aatgcgttag cttactacaa cacaacaaag ggaggtaggt    12720
ttgtacttgc actgttatcc gatttacagg atttgaaatg ggctagattc cctaagagtg    12780
atggaactgg tactatctat acagaactgg aaccaccttg taggtttgtt acagacacac    12840
ctaaaggtcc taaagtgaag tatttatact ttattaaagg attaaacaac ctaaatagag    12900
gtatggtact tggtagttta gctgccacag tacgtctaca agctggtaat gcaacagaag    12960
tgcctgccaa ttcaactgta ttatcttcct gtgcttttgc tgtagatgct gctaaagctt    13020
acaaagatta tctagctagt gggggacaac caatcactaa ttgtgttaag atgttgtgta    13080
cacacactgg tactggtcag gcaataacag ttacaccgga agccaatatg gatcaagaat    13140
cctttggtgg tgcatcgtgt tgtctgtact gccgttgcca catagatcat ccaaatccta    13200
aaggattttg tgacttaaaa ggtaagtatg tacaaatacc tacaacttgt gctaatgacc    13260
ctgtgggttt tacacttaaa aacacagtct gtaccgtctg cggtatgtgg aaaggttatg    13320
gctgtagttg tgatcaactc cgcgaaccca tgcttcagtc agctgatgca caatcgtgca    13380
gcactagtac tgatgtcgta tacagggctt tgacatctct caatgataaa gtagctggtt    13440
ttgctaaatt cctaaaaact aattgttgtc gcttccaaga aaaggacgaa gatgacaatt    13500
taattgattc ttactttgta gttaagagac acactttctc taactaccaa catgaagaaa    13560
caatttataa tttacttaag gattgtccag ctgttgctaa acatgacttc tttaagttta    13620
gaatagacgg tgacatggta ccacatatat cacgtcaacg tcttactaaa tacacaatgg    13680
cagacctcgt ctatgcttta aggcattttg atgaaggtaa ttgtgacaca ttaaaagaaa    13740
tacttgtcat tcaataaaaa ggactggtat gattttgtag aaaacccaga tatattacgc    13800
gtatacgcca acttaggtga acgtgtacgc caagctttgt taaaaacagt acaattctgt    13860
gatgccatgc gaaatgctgg tattgttggt gtactgacat tagataatca agatctcaat    13920
ggtaactggt atgatttcgg tgatttcata caaccacgc caggtagtgg agttcctgtt    13980
gtagattctt attattcatt gttaatgcct atattaacct tgaccagggc tttaactgca    14040
gagtcacatg ttgacactga cttaacaaag ccttacatta gtgggatttg gttaaaatat    14100
gacttcacgg aagagaggtt aaaactcttt gaccgttatt ttaaatattg ggatcagaca    14160
taccacccaa attgtgttaa ctgtttggat gacagatgca ttctgcattg tgcaaacttt    14220
aatgttttat tctctacagt gttcccactt acaagttttg gaccactagt gagaaaaata    14280
tttgttgatg gtgttccatt tgtagtttca actggatacc acttcagaga gctaggtgtt    14340
gtacataatc aggatgtaaa cttacatagc tctagactta gttttaagga attacttgtg    14400
tatgctgctg accctgctat gcacgctgct tctggtaatc tattactaga taaacgcact    14460
acgtgctttt cagtagctgc acttactaac aatgttgctt ttcaaactgt caaacccggt    14520
```

```
aattttaaca aagacttcta tgactttgct gtgtctaagg gtttctttaa ggaaggaagt   14580
tctgttgaat taaaacactt cttctttgct caggatggta atgctgctat cagcgattat   14640
gactactatc gttataatct accaacaatg tgtgatatca gacaactact atttgtagtt   14700
gaagttgttg ataagtactt tgattgttac gatggtggct gtattaatgc taaccaagtc   14760
atcgtcaaca acctagacaa atcagctcta ggatcaagat gcacttttcg catatacaaa   14820
acgtaatgtc aatgccatta gtgcaaagaa tagagctcgc accgtagctg gtgtctctat   14880
ctgtagtact atgaccaata gacagtttca tcaaaaatta ttgaaatcaa tagccgccac   14940
tagaggagct actgtagtaa ttggaacaag caaattctat ggtggttggc acaacatgtt   15000
aaaaactgtt tatagtgatg tagaaaaccc tcaccttatg ggttgggatt atcctaaatg   15060
tgatagagcc atgcctaaca tgcttagaat tatggcctca cttgttcttg ctcgcaaaca   15120
tacaacgtgt tgtagcttgt cacaccgttt ctatagatta gctaatgagt gtgctcaagt   15180
attgagtgaa attgtcatgt gtggcggttc actatatgtt aaaccaggtg aacctcatc   15240 aggagatgcc acaactgctt atgctaatag tgttttttaac atttgtcaag ctgtcacggc   15300
caatgttaat gcacttttat ctactgatgg taacaaaatt gccgataagt atgtccgcaa   15360
tttacaacac agactttatg agtgtctcta tagaaataga gatgttgaca cagactttgt   15420
gaatgagttt tacgcatatt tgcgtaaaca tttctcaatg atgatactct ctgacgatgc   15480
tgttgtgtgt ttcaatagca cttatgcatc tcaaggtcta gtggctagca taagaacttt   15540
taagtcagtt cttttattatc aaaacaatgt ttttatgtct gaagcaaaat gttggactga   15600
gactgaccct actaaaggac ctcatgaatt ttgctctcaa catacaatgc tagttaaaca   15660
gggtgatgat tatgtgtacc ttccttaccc agatccatca agaatcctag gggccggctg   15720
ttttgtagat gatatcgtaa aaacagatgg tacacttatg attgaacggt tcgtgtcttt   15780
agctatagat gcttacccac ttactaaaca tcctaatcag gagtatgctg atgtctttca   15840
tttgtactta caatacataa gaaagctaca tgatgagtta acaggacaca tgttagacat   15900
gtattctgtt atgcttacta atgataacac ttcaaggtat tgggaacctg agttttatga   15960
ggctatgtac acaccgcata cagtcttaca ggctgttggg gcttgtgttc tttgcaattc   16020 acagactta ttaagatgtg gtgcttgcat acgtagacca ttcttatgtt gtaaatgctg   16080
ttacgaccat gtcatatcaa catcacataa attagtcttg tctgttaatc cgtatgtttg   16140
caatgctcca ggttgtgatg tcacagatgt gactcaactt tacttaggag gtatgagcta   16200
ttattgtaaa tcacataaac cacccattag ttttccattg tgtgctaatg acaagttttt   16260
tggtttatat aaaaatacat gtgttggtag cgataatgtt actgacttta atgcaattgc   16320
aacatgtgac tggacaaatg ctggtgatta cattttagct aacacctgta ctgaaagact   16380
caagcttttt gcagcagaaa cgctcaaagc tactgaggag acatttaaac tgtcttatgg   16440
tattgctact gtacgtgaag tgctgtctga cagagaatta catctttcat gggaagttgg   16500
taaacctaga ccaccactta accgaaatta tgtctttact ggttatcgtg taactaaaaa   16560
cagtaaagta caaataggag agtacacctt tgaaaaaggt gactatggtg atgctgttgt   16620
ttaccgaggt acaacaactt acaaattaaa tgttggtgat tattttgtgc tgacatcaca   16680
tacagtaatg ccattaagtg cacctacact agactggctt ataccccaaca ctcaatatct   16740 cagatgagtt ttctagcaat gttgcaaatt atcaaaaggt tggtatgcaa aagtattcta   16800
cactccaggg accacctggt actggtaaga gtcatttttgc tattggccta gctctctact   16860
```

```
accccttctgc tcgcatagtg tatacagctt gctctcatgc cgctgttgat gcactatgtg    16920
agaaggcatt aaaatatttg cctatagata aatgtagtag aattatacct gcacgtgctc    16980
gtgtagacag tatgtctttt gtactgtaaa tgcattgcct gagacgacag cagatatagt    17040
tgtctttgat gaaatttcaa tggccacaaa ttatgatttg agtgttgtca atgccagatt    17100
acgtgctaag cactatgtgt acattggcga ccctgctcaa ttacctgcac cacgcacatt    17160
gctaactaag ggcacactag aaccagaata tttcaattca gtgtgtagac ttatgaaaac    17220
tataggtcca gacatgttcc tcggaacttg tcggcgttgt cctgctgaaa ttgttgacac    17280
tgtgagtgct ttggtttatg ataataagct taaagcacat aaagacaaat cagctcaatg    17340 cttttaaaatg ttttataagg gtgttatcac gcatgatgtt tcatctgcaa ttaacaggcc    17400
acaaataggc gtggtaagag aattccttac acgtaaccct gcttggagaa aagctatgct    17460
gtagcctcaa agattttggg actaccaact caaactgttg attcatcaca gggctcagaa    17520
tatgactatg tcatattcac tcaaaccact gaaacagctc actcttgtaa tgtaaacaga    17580
tttaatgttg ctattaccag agcaaaagta ggcatacttt gcataatgtc tgatagagac    17640
ctttatgaca agttgcaatt tacaagtctt gaaattccac gtaggaatgt ggcaacttta    17700
caagctgaaa atgtaacagg actctttaaa gattgtagta aggtaatcac tgggttacat    17760
cctacacagg cacctacaca cctcagtgtt gacactaaat tcaaaactga aggtttatgt    17820
gttgacatac ctgcataccc taaggacatg acctatagaa gactcatctc tatgatgggg    17880
tttaaaatga attatcaagt taatggttac cctaacatgt ttatcacccg cgaagaagct    17940
ataagacatg tacgtgcatg gattggcttc gatgtcgagg ggtgtcatgc tactagagaa    18000
gctgttggta ccaatttacc tttacagcta ggttttttcta caggtgttaa cctagttgct    18060
gtacctacag gttatgttga tacacctaat aatacagatt tttccagagt tagtgctaaa    18120
ccaccgcctg gagatcaatt taaacacctc ataccactta tgtacaaagg acttccttgg    18180
aatgtagtgc gtataaagat tgtacaaatg ttaagtgaca cacttaaaaa tctctctgac    18240
agagtcgtat ttgtcttatg ggcacatggc tttgagttga catctatgaa gtattttgtg    18300
aaaataggac ctgagcgcac ctgttgtcta tgtgatagac gtgccacatg ctttttccact    18360 gcttcagaca cttatgcctg ttggcatcat tctattggat ttgattacgt ctataatccg    18420
tttatgattg atgttcaaca atgggggtttt acaggtaacc tacaaagcaa ccatgatctg    18480
tattgtcaag tccatggtaa tgcacatgta gctagttgtg atgcaatcat gactaggtgt    18540
ctagcttgac tggactattg aatatcctat aattggtgat gaactgaaga ttaatgcggc    18600
ttgtagaaag gttcaacaca tggttgttaa agctgcatta ttagcagaca aattcccagt    18660
tcttcacgac attggtaacc ctaaagctat taagtgtgta cctcaagctg atgtagaatg    18720
gaagttctat gatgcacagc cttgtagtga caaagcttat aaaatagaag aattattcta    18780
ttcttatgcc acacattctg acaaattcac agatggtgta tgcctatttt ggaattgcaa    18840
tgtcgataga tatcctgcta attccattgt ttgtagattt gacactagag tgctatctaa    18900
ccttaacttg cctggttgtg atggtggcag tttgtatgta aataaacatg cattccacac    18960
accagctttt gataaaagtg ctttttgtaa ttttaaacaa ttaccatttt tctattactc    19020
tgacagtcca tgtgagtctc atggaaaaca agtagtgtca gatatagatt atgtaccact    19080
aaagtctgct acgtgtataa cacgttgcaa tttaggtggt gctgtctgta gacatcatgc    19140
taatgagtac agattgtatc tcgatgctta taacatgatg atctcagctg ctttagctt    19200 gtgggtttac aaacaatttg atacttataa cctctggaac acttttacaa gacttcagag    19260
```

```
tttagaaaat gtggctttta atgttgtaaa taagggacac tttgatggac aacagggtga   19320
agtaccagtt tctatcatta ataacactgt ttacacaaaa gttgatggtg ttgatgtaga   19380
attgtttgaa aataaaacaa cattacctgt taatgtagca tttgagcttt gggctaagcg   19440
caacattaaa ccagtaccag aggtgaaaat actcaataat ttgggtgtgg acattgctgc   19500
taatactgtg atctgggact acaaaagaga tgctccagca catatatcta ctattggtgt   19560
ttgttctatg actgacatag ccaagaaacc aactgaaacg atttgtgcac cactcactgt   19620 ctttttgat ggtagagttg atggtcaagt agacttattt agaaatgccc gtaatggtgt   19680
tcttattaca gaaggtagtg ttaaaggttt acaaccatct gtaggtccca aacaagctag   19740
tcttaatgga gtcacattaa ttggagaagc cgtaaaaaca cagttcaatt attataagaa   19800
agttgatggt gttgtccaac aattacctga aacttacttt actcagagta gaaatttaca   19860
agaatttaaa cccaggagtc aaatggaaat tgatttctta gaattagcta tggatgaatt   19920
cattgaacgg tataaattag aaggctatgc cttcgaacat atcgtttatg gagatttag   19980 tcatagtcag ttaggtggtt tacatctact gattggacta gctaaacgtt ttaaggaatc   20040
accttttgaa ttagaagatt ttattcctat ggacagtaca gttaaaaact atttcataac   20100
agatgcgcaa acaggttcat ctaagtgtgt gtgttctgtt attgatttat acttgatga    20160 ttttgttgaa ataataaaat cccaagattt atctgtagtt tctaaggttg tcaaagtgac   20220
tattgactat acagaaattt catttatgct ttggtgtaaa gatggccatg tagaaacatt   20280
ttacccaaaa ttacaatcta gtcaagcgtg gcaaccgggt gttgctatgc ctaatctta   20340 caaaatgcaa agaatgctat tagaaaagtg tgaccttcaa aattatggtg atagtgcaac   20400
attacctaaa ggcatactgt gtcaatattt aaacacatta acattagctg taccctataa   20460
tatgagagtt atacattttg gtgctggttc tgataaagga gttgcaccag gtacagctgt   20520
tttaagacag tggttgccta cgggtacgct gcttgtcgat tcagatctta atgactttgt   20580
ctctgatgca gattcaactt tgattggtga ttgtgcaact gtacatacag ctaataaatg   20640
ggatctcatt attagtgata tgtacgaccc taagactaaa aatgttacaa agaaaaatga   20700
ctctaaagag ggttttttca cttacatttg tgggtttata caacaaaagc tagctcttgg   20760
aggttccgtg gctataaaga taacagaaca ttcttggaat gctgatcttt ataagctcat   20820
gggacacttc gcatggtgga cagcctttgt tactaatgtg aatgcgtcat catctgaagc   20880 attttttaatt ggatgtaatt atcttggcaa accacgcgaa caaatagatg gttatgtcat   20940
gcatgcaaat tacatatttt ggaggaatac aaatccaatt cagttgtctt cctattcttt   21000
atttgacatg agtaaatttc cccttaaatt aaggggtact gctgttatgt ctttaaagga   21060
aggtcaaatc aatgatatga ttttatctct tcttagtaaa ggtagactta taattagaga   21120
aaacaacaga gttgttattt ctagtgatgt tcttgttaac aactaaacga acaatgtttg   21180
tttttcttgt tttattgcca ctagtctcta gtcagtgtgt taatcttaca accagaactc   21240
aattaccccc tgcatacact aattctttca cacgtggtgt ttattaccct gacaaagttt   21300
tcagatcctc agttttacat tcaactcagg acttgttctt acctttcttt tccaatgtta   21360
cttggttcca tgctatacat gtctctggga ccaatggtac taagaggttt gataaccctg   21420
tcctaccatt taatgatggt gtttattttg cttccactga gaagtctaac ataataagag   21480
gctggatttt tggtactact ttagattcga agacccagtc cctacttatt gttaataacg   21540
ctactaatgt tgttattaaa gtctgtgaat ttcaattttg taatgatcca tttttgggtg   21600
```

```
tttattacca caaaaacaac aaaagttgga tggaaagtga gttcagagtt tattctagtg    21660
cgaataattg cacttttgaa tatgtctctc agccttttct tatggacctt gaaggaaaac    21720
agggtaattt caaaaatctt agggaatttg tgtttaagaa tattgatggt tatttttaaaa   21780 tatattctaa gcacacgcct attaatttag tgcgtgatct ccctcagggt ttttcggctt    21840
tagaaccatt ggtagatttg ccaataggta ttaacatcac taggtttcaa actttacttg    21900
ctttacatag aagttatttg actcctggtg attcttcttc aggttggaca gctggtgctg    21960
cagcttatta tgtgggttat cttcaaccta ggacttttct attaaaatat aatgaaaatg    22020
gaaccattac agatgctgta gactgtgcac ttgaccctct ctcagaaaca aagtgtacgt    22080
tgaaatcctt cactgtagaa aaggaatct atcaaacttc taactttaga gtccaaccaa     22140
cagaatctat tgttagattt cctaatatta caaacttgtg ccctttggt gaagtttta      22200 acgccaccag atttgcatct gtttatgctt ggaacaggaa gagaatcagc aactgtgttg    22260
ctgattattc tgtcctatat aattccgcat catttccac ttttaagtgt tatggagtgt     22320
ctcctactaa attaaatgat ctctgcttta ctaatgtcta tgcagattca tttgtaatta    22380
gaggtgatga agtcagacaa atcgctccag gcaaactgg aaagattgct gattataatt     22440
ataaattacc agatgatttt acaggctgcg ttatagcttg gaattctaac aatcttgatt    22500
ctaaggttgg tggtaattat aattacctgt atagattgtt taggaagtct aatctcaaac    22560
cttttgagag agatatttca actgaaatct atcaggccgg tagcacacct tgtaatggtg    22620
ttgaaggttt taattgttac ttcccttac aatcatatgg tttccaaccc actaatggtg     22680
ttggttacca accatacaga gtagtagtac tttcttttga acttctacat gcacctgcaa    22740
ctgtttgtgg acctaaaaag tctactaatt tggttaaaaa caatgtgtc aatttcaact     22800 tcaatggttt aacaggcaca ggtgttctta ctgagtctaa caaaaagttt ctgccttcc     22860 aacaatttgg cagagacatt gctgacacta ctgatgctgt ccgtgatcca cagacacttg    22920
agattcttga cattacacca tgttcttttg gtggtgtcag tgtttataaca ccaggaacaa   22980 atacttctaa ccaggttgct gttctttatc agggtgttaa ctgcacagaa gtccctgttg    23040
ctattcatgc agatcaactt actcctactt ggcgtgttta ttctacaggt tctaatgttt    23100
ttcaaacacg tgcaggctgt ttaataggg ctgaacatgt caacaactca tatgagtgtg     23160
acatacccat tggtgcaggt atatgcgcta gttatcagac tcagactaat tctcctcggc    23220
gggcacgtag tgtagctagt caatccatca ttgcctacac tatgtcactt ggtgcagaaa    23280
attcagttgc ttactctaat aactctattg ccatacccac aaattttact attagtgtta    23340
ccacagaaat tctaccagtg tctatgacca agacatcagt agattgtaca atgtacattt    23400
gtggtgattc aactgaatgc agcaatcttt tgttgcaata tggcagtttt tgtacacaat    23460
taaaccgtgc tttaactgga ataactgttg aacaagacaa aaacacccaa gaagtttttg    23520
cacaagtcaa acaaatttac aaaacaccac caattaaaga ttttggtggt tttaattttt    23580
cacaaatatt accagatcca tcaaaaccaa gcaagaggtc atttattgaa gatctacttt    23640
tcaacaaagt gacacttgca gatgctggct tcatcaaaca atatggtgat tgccttggtg    23700
atattgctgc tagagacctc atttgtgcac aaaagtttaa cggccttact gtttttgccac   23760 ctttgctcac agatgaaatg attgctcaat acacttctgc actgttagcg ggtacaatca    23820
cttctggttg gacctttggt gcaggtgctg cattacaaat accatttgct atgcaaatgg    23880
cttataggtt taatggtatt ggagttacac agaatgttct ctatgagaac caaaaattga    23940
ttgccaacca atttaatagt gctattggca aaattcaaga ctcactttct tccacagcaa    24000
```

```
gtgcacttgg aaaacttcaa gatgtggtca accaaaatgc acaagcttta aacacgcttg   24060
ttaaacaact tagctccaat tttggtgcaa tttcaagtgt tttaaatgat atcctttcac   24120
gtcttgacaa agttgaggct gaagtgcaaa ttgataggtt gatcacaggc agacttcaaa   24180
gtttgcagac atatgtgact caacaattaa ttagagctgc agaaatcaga gcttctgcta   24240
atcttgctgc tactaaaatg tcagagtgtg tacttggaca atcaaaaaga gttgatttt    24300 gtggaaaggg ctatcatctt atgtccttcc ctcagtcagc acctcatggt gtagtcttct   24360
tgcatgtgac ttatgtccct gcacaagaaa agaacttcac aactgctcct gccatttgtc   24420
atgatggaaa agcacacttt cctcgtgaag gtgtctttgt ttcaaatggc acacactggt   24480
ttgtaacaca aaggaattt  tatgaaccac aaatcattac tacagacaac acatttgtgt   24540
ctggtaactg tgatgttgta ataggaattg tcaacaacac agtttatgat cctttgcaac   24600
ctgaattaga ctcattcaag gaggagttag ataaatattt taagaatcat acatcaccag   24660
atgttgattt aggtgacatc tctggcatta atgcttcagt tgtaaacatt caaaaagaaa   24720
ttgaccgcct caatgaggtt gccaagaatt taaatgaatc tctcatcgat ctccaagaac   24780
ttggaaagta tgagcagtat ataaaatggc catggtacat ttggctaggt tttatagctg   24840
gcttgattgc catagtaatg gtgacaatta tgctttgctg tatgaccagt tgctgtagtt   24900
gtctcaaggg ctgttgttct tgtggatcct gctgcaaatt tgatgaagac gactctgagc   24960
cagtgctcaa aggagtctat ggatttgttt atgagaatct tcacaattgg aactgtaact   25020
ttgaagcaag gtgaaatcaa ggatgctact ccttcagatt tgttcgcgc  tactgcaacg   25080 ataccgatac aagcctcact cccttcgga tggcttattg ttggcgttgc acttcttgct    25140 gttttcaga gcgcttccaa aatcataacc ctcaaaaaga gatggcaact agcactctcc    25200
aagggtgttc actttgtttg caacttgctg ttgttgtttg taacagttta ctcacacctt   25260
ttgctcgttg ctgctggcct tgaagcccct tttctctatc tttatgcttt agtctacttc   25320
ttgcagagta taaactttgt aagaataata atgaggcttt ggctttgctg taaatgccgt   25380
tccaaaaacc cattacttta tgatgccaac tattttcttt gctggcatac taattgttac   25440
gactattgta taccttacaa tagtgtaact tcttcaattg tcattacttc aggtgatggc   25500
acaacaagtc ctattctga  acatgactac cagattggtg ttatactga  aaaatgggaa   25560 tctggagtaa aagactgtgt tgtattacac agttacttca cttcagacta ttaccagctg   25620
tactcaactc aattgagtac agacactggt gttgaacatg ttaccttctt catctacaat   25680
aaaattgttg atgagcctga agaacatgtc caaattcaca caatcgacgg ttcatccgga   25740
gttgttaatc cagtaatgga accaattat  gatgaaccga cgacgactac tagcgtgcct   25800
ttgtaagcac aagctgatga gtacgaactt atgtactcat tcgtttcgga agagacaggt   25860
acgttaatag ttaatagcgt acctagttac actagccatc cttactgcgc ttcgattgtg   25920
tgcgtactgc tgcaatattg ttaacgtgag tcttgtaaaa ccttcttttt acgtttactc   25980
tcgtgttaaa aatctgaatt cttctagagt tcctgatctt ctggtctaaa cgaactaaat   26040
attatattag ttttttctgtt tggaacttta atttagcca tggcagattc caacggtact   26100
attaccgttg aagagcttaa aaagctcctt gaacaatgga acctagtaat aggtttccta   26160
ttccttacat ggatttgtct tctacaattt gcctatgcca acaggaatag gttttttgtat  26220 ataattaagt taatttttcct ctggctgtta tggccagtaa ctttagcttg ttttgtgctt  26280
gctgctgttt acagaataaa ttggatcacc ggtggaattg ctatcgcaat ggcttgtctt   26340
```

```
gtaggcttga tgtggctcag ctacttcatt gcttctttca gactgtttgc gcgtacgcgt   26400
tccatgtggt cattcaatcc agaaactaac attcttctca acgtgccact ccatggcact   26460
attctgacca gaccgcttct agaaagtgaa ctcgtaatcg gagctgtgat ccttcgtgga   26520
catcttcgta ttgctggaca ccatctagga cgctgtgaca tcaaggacct gcctaaagaa   26580
atcactgttg ctacatcacg aacgctttct tattacaaat gggagcttc gcagcgtgta    26640 gcaggtgact caggttttgc tgcatacagt cgctacagga ttggcaacta taaattaaac   26700
acagaccatt ccagtagcag tgacaatatt gctttgcttg tacagtaagt gacaacagat   26760
gtttcatctc gttgactttc aggttactat agcagagata ttactaatta ttatgaggac   26820
ttttaaagtt tccatttgga atcttgatta catcataaac ctcataatta aaaatttatc   26880
taagtcacta actgagaata aatattctca attagatgaa gagcaaccaa tggagattga   26940
ttaaacgaac atgaaaatta ttcttttctt ggcactgata acactcgcta cttgtgagct   27000
ttatcactac caagagtgtg ttagaggtac aacagtactt ttaaaagaac cttgctcttc   27060
tggaacatac gagctgataa caaatttgca ctgacttgct ttagcactca atttgctttt   27120
gcttgtcctg acggcgtaaa acacgtctat cagttacgtg ccagatcagt ttcacctaaa   27180
ctgttcatca gacaagagga agttcaagaa ctttactctc caattttct tattgttgcg    27240 gcaatagtgt ttataacact ttgcttcaca ctcaaaagaa agacagaatg attgaacttt   27300
cattaattga cttctatttg tgcttttag cctttctgct attccttgtt ttaattatgc     27360
ttattatctt ttggttctca cttgaactgc aagatcataa tgaaacttgt cacgcctaaa   27420
cgaacatgaa atttcttgtt ttcttaggaa tcatcacaac tgtagctgca tttcaccaag   27480
aatgtagttt acagtcatgt actcaacatc aaccatatgt agttgatgac ccgtgtccta   27540
ttcacttcta ttctaaatgg tatattagag taggagctag aaaatcagca cctttaattg   27600
aattgtgcgt ggatgaggct ggttctaaat cacccattca gtacatcgat atcggtaatt   27660
atacagtttc ctgtttacct tttacaatta attgccagga acctaaattg ggtagtcttg   27720
tagtgcgttg ttcgttctat gaagactttt tagagtatca tgacgttcgt gttgttttag   27780
attctgataa tggaccccaa aatcagcgaa atgcaccccg cattacgttt ggtggaccct   27840
cagattcaac tggcagtaac cagaatggag aacgcagtgg ggcgcgatca aaacaacgtc   27900
ggccccaagg tttacccaat aatactgcgt cttggttcac cgctctcact caacatggca   27960
aggaagacct taaattccct cgaggacaag gcgttccaat taacaccaat agcagtccag   28020
atgaccaaat tggctactac cgaagagcta ccagacgaat tcgtggtggt gacggtaaaa   28080
tgaaagatct cagtccaaga tggtatttct actacctagg aactgggcca aagctggac    28140 ttccctatgg tgctaacaaa gacggcatca tatgggttgc aactgaggga gccttgaata   28200
caccaaaaga tcacattggc acccgcaatc ctgctaacaa tgctgcaatc gtgctacata   28260
cgcagaaggg agcagaggcg gcagtcaagc ctcttctcgt tcctcatcac gtagtcgcaa   28320
catttcaaga aattcaactc caggcagcag taaacgaact tctcctgcta gaatggctgg   28380
caatggcggt gatgctgctc ttgctttgct gctgcttgac agattgaacc agcttgagag   28440
caaaatgtac tgtcactaag aaatctgctg ctgaggcttc taagaagcct cggcaaaaac   28500
gtactgccac taaagcatac aatgtaacac aagctttcgg cagacgtcag gaactaatca   28560
gacaaggaac tgattacaaa cattggccgc aaattgcaca atttgccccc agcgcttcag   28620
cgttcttcgg aatgtcgcgc attggcatgg aagtcacacc ttcgggaacg tggttgacct   28680
acacaggtgc catcaaattg gatgacaaag atccaaattt caaagatcaa gtcattttgc   28740
```

```
tgaataagca tattgacgca tggacaaaaa gaagaaggct gatgaaactc aagccttacc  28800
gcagagacag aagaaacagc aaactgtgac tcttcttcct gctgcagatt tggatgattt  28860
ctccaaacaa ttgcaacaat ccatgagcag tgctgactca actcaggcct aaactcatgc  28920
agaccacaca aggcagatgg gctatataaa cgttttcgct tttccgttta cgatatatag  28980
tctactcttg tgcagaatga attctcgtaa ctacatagca caagtagatg tagttaactt  29040
taatctcaca tagcaatctt taatcagtgt gtaacattag ggaggactag gccacgcgga  29100
gtacgatcga gtgtacagtg aacaatgcta gggagagctt aaaattaatt ttagtagtgc  29160
tatccccatg tgattttaat agcttcttag gagaatgaca aaaaaaaaa aaaaaaaaa  29220 aaaaaaaaa aaaaaaaaa aaaaaaaaa aaaa                               29254
```

Having described my invention herein, I claim:

1. A composition comprised of statistically significant DNA fragments consisting of the sequences SEQ ID NOs: 1-92 encapsulated in an appropriate delivery system.

2. A composition comprised of statistically significant mRNA fragments consisting of the sequences SEQ ID NOs: 93-184 encapsulated in an appropriate delivery system.

3. A composition comprising a SARS-CoV 2 genome represented by SEQ ID NO: 185, where one or more of SEQ ID NOs: 1-92 have been removed from the genome.

* * * * *